(12) United States Patent
Bodoc et al.

(10) Patent No.: US 11,497,689 B2
(45) Date of Patent: *Nov. 15, 2022

(54) THICKENING SELF-INVERTIBLE INVERSE LATEX COMPRISING, AS AN INVERTING AGENT, SURFACTANT SPECIES OF THE POLYGLYCEROL ESTER FAMILY, AND COMPOSITIONS CONTAINING SAME

(71) Applicant: SOCIETE D'EXPLOITATION DE PRODUITS POUR LES INDUSTRIES CHIMIQUES SEPPIC, Paris (FR)

(72) Inventors: Miruna Bodoc, Lavaur (FR); Jérôme Guilbot, Castres (FR); Georges Da Costa, Saix (FR); Aurélie Colas, Marly le Roi (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 7 days.

This patent is subject to a terminal disclaimer.

(21) Appl. No.: 16/977,568

(22) PCT Filed: Feb. 27, 2019

(86) PCT No.: PCT/FR2019/050443
§ 371 (c)(1),
(2) Date: Sep. 2, 2020

(87) PCT Pub. No.: WO2019/170979
PCT Pub. Date: Sep. 12, 2019

(65) Prior Publication Data
US 2021/0007962 A1 Jan. 14, 2021

(30) Foreign Application Priority Data

Mar. 6, 2018 (FR) ...................................... 1851933

(51) Int. Cl.
| | | |
|---|---|---|
| C08F 220/38 | (2006.01) | |
| C08F 220/06 | (2006.01) | |
| A61K 8/06 | (2006.01) | |
| A61K 8/81 | (2006.01) | |
| C08L 33/26 | (2006.01) | |
| C08F 220/58 | (2006.01) | |
| C08F 222/38 | (2006.01) | |

(52) U.S. Cl.
CPC ............ *A61K 8/064* (2013.01); *A61K 8/8158* (2013.01); *C08F 220/06* (2013.01); *C08F 220/585* (2020.02); *C08F 222/385* (2013.01); *C08L 33/26* (2013.01); *A61K 2800/10* (2013.01); *A61K 2800/48* (2013.01)

(58) Field of Classification Search
CPC ................ C08F 220/06; C08F 220/585; C08F 222/385; A61K 8/064
See application file for complete search history.

(56) References Cited

U.S. PATENT DOCUMENTS

| | | | |
|---|---|---|---|
| 6,278,008 B1 | 8/2001 | Endo et al. | |
| 6,375,959 B1 | 4/2002 | Mallo et al. | |
| 2011/0076245 A1* | 3/2011 | Braun | A61K 8/33 424/59 |
| 2011/0098364 A1 | 4/2011 | Braun et al. | |
| 2014/0248321 A1* | 9/2014 | Amalric | A61Q 19/007 424/401 |

FOREIGN PATENT DOCUMENTS

| | | |
|---|---|---|
| EP | 0 971 683 | 1/2000 |
| EP | 1 055 451 | 11/2000 |
| EP | 1 515 688 | 3/2005 |
| FR | 2 794 034 | 12/2000 |
| FR | 2 794 124 | 12/2000 |
| FR | 2 808 446 | 11/2001 |
| FR | 2 808 447 | 11/2001 |
| FR | 2 810 883 | 1/2002 |
| TW | 201212943 A1 | 4/2012 |
| WO | 96/00719 | 1/1996 |
| WO | 98/44902 | 10/1998 |
| WO | 03/103616 | 12/2003 |
| WO | 2009/156691 | 12/2009 |

OTHER PUBLICATIONS

International Search Report for PCT/FR2019/050443 dated May 10, 2019, 6 pages, with English Translation.
Written Opinion of the ISA for PCT/FR2019/050443 dated May 10, 2019, 8 pages.
French Search Report for French Application No. 1851933 dated Nov. 12, 2018, 2 pages.

* cited by examiner

Primary Examiner — Karuna P Reddy
(74) Attorney, Agent, or Firm — Nixon & Vanderhye

(57) ABSTRACT

Disclosed is a self-invertible inverse latex including, as an inverting agent, surfactant species of the polyglycerol ester family; the use thereof as a thickening and/or emulsifying and/or stabilising agent for a cosmetic, dermopharmaceutical or pharmaceutical topical composition, and cosmetic, dermopharmaceutical or pharmaceutical topical compositions containing same. Also disclosed is a new surfactant composition containing polyglycerol esters.

10 Claims, No Drawings

US 11,497,689 B2

THICKENING SELF-INVERTIBLE INVERSE LATEX COMPRISING, AS AN INVERTING AGENT, SURFACTANT SPECIES OF THE POLYGLYCEROL ESTER FAMILY, AND COMPOSITIONS CONTAINING SAME

CROSS-REFERENCE TO RELATED APPLICATIONS

This application is the U.S. national phase of International Application No. PCT/FR2019/050443 filed Feb. 27, 2019 which designated the U.S. and claims priority to French Application No. 1851933 filed Mar. 6, 2018, the entire contents of each of which are hereby incorporated by reference.

BACKGROUND OF THE INVENTION

Field of the Invention

The invention relates to self-invertible inverse latexes comprising, as inverting agent, a surfactant composition comprising esters of polyglycerols and glycerol and/or glycerol oligomers, to the use of said self-invertible inverse latexes as thickeners used to prepare cosmetic or pharmaceutical formulations for topical use, as well as to said formulations thus prepared.

Description of the Related Art

Cosmetic and pharmaceutical compositions for topical use, comprising polar phases, such as, for example, aqueous, alcoholic, aqueous/alcoholic or aqueous/glycolic phases, frequently require the use of rheology-modifying polymers to increase the viscosity of said polar phases, and more generally to confer on them a specific rheological behavior. Rheology modifiers provide both an increase in the viscosity of the polar phase, as well as a degree of consistency of and/or a stabilizing effect on the composition for topical use to be thickened.

The rheology-modifying agents which can be used for the preparation of these compositions for topical use include synthetic polymers, such as, for example, anionic or cationic or ampholytic polyelectrolytes, which are linear or branched and crosslinked or noncrosslinked, exist in two physical forms, the powder form and the liquid form.

Said cosmetic and pharmaceutical compositions for topical use are generally provided in the form of aqueous gels, of aqueous/alcoholic gels, of aqueous/glycolic gels, of emulsions or of microemulsions or of nanoemulsions of water-in-oil type or of oil-in-water type or of water-in-oil-in-water type or of oil-in-water-in-oil type.

The anionic or cationic or ampholytic polyelectrolytes, which are linear or branched and crosslinked or noncrosslinked, provided in a liquid form, include those known under the name of "self-invertible inverse latexes", which are emulsions of water-in-oil type comprising the polyelectrolyte, an aqueous phase, a fatty phase composed of at least one oil, at least one emulsifier of water-in-oil type and at least one emulsifier of oil-in-water type. In processes for the preparation of self-invertible inverse latexes by the use of an inverse emulsion radical polymerization, the surfactants of oil-in-water type are added on conclusion of the polymerization stage. The purpose of their addition is to modify and to adjust the hydrophilic/lipophilic balance of the water-in-oil emulsion comprising the polymer (also known as "inverse latex") so as to obtain a mixture which, once added to a polar phase, such as, for example, water, will change emulsion direction in order to pass from the water-in-oil form to the oil-in-water form, then making it possible to bring the polymer prepared previously into contact with the polar phase to be thickened. During such a physical phenomenon, the polymer of crosslinked and/or branched polyelectrolyte type spreads out in said polar phase and forms a three-dimensional network making it possible for the polar phase to swell, which is manifested by an increase in the viscosity of this polar phase. The mixture comprising the "inverse latex" and the surfactant of oil-in-water type is known as self-invertible inverse latex and said surfactant of oil-in-water type is known as "inverter" or "inverting agent".

The inverting agents commonly used for the preparation of self-invertible inverse latexes are surface-active agents of oil-in-water type which have an HLB (hydrophilic/lipophilic balance) value which is sufficiently high to make it possible to prepare stable emulsions of oil-in-water type, generally of greater than 9 and less than 16. They generally comprise a hydrophilic part consisting of a sequence of ethylene oxide units and a part consisting of an aliphatic hydrocarbon chain of hydrophobic nature. These inverting agents include:

ethoxylated fatty alcohols, the aliphatic hydrocarbon chain of which comprises from 8 to 14 carbon atoms and the number of ethylene oxide units of which is between 5 and 40, for example ethoxylated lauryl alcohol comprising 7 mol of ethylene oxide (INCI name: Laureth-7) or tridecyl alcohol comprising 6 mol of ethylene oxide (INCI name: Trideceth-6);

ethoxylated sorbitan esters, the aliphatic hydrocarbon chain of which comprises from 12 to 22 carbon atoms and the number of ethylene oxide units of which is between 5 and 40, for example ethoxylated sorbitan oleate comprising 20 mol of ethylene oxide, sold under the trade name Montanox™ 80, or ethoxylated sorbitan laurate comprising 20 mol of ethylene oxide, sold under the trade name Montanox™ 20;

ethoxylated alkylphenols, for example ethoxylated nonylphenols and ethoxylated octylphenols; or ethoxylated castor oils, for example ethoxylated castor oil comprising 40 mol of ethylene oxide, sold under the brand name Simulsol™ OL 50.

Changes in consumer demands and in regulatory provisions have led cosmetic composition formulators to reduce the proportion of ingredients comprising ethylene oxide units in their formulations. There thus exists a need to prepare self-invertible inverse latexes which are devoid of ethoxylated surfactants as inverting agents.

The French patent applications published under the numbers 2 794 034, 2 794 124, 2 808 447, 2 808 446 and 2 810 883 describe the use of alkyl polyglycosides, the hydrocarbon alkyl chain of which comprises from 1 to 30 carbon atoms, as inverting agents for preparing self-invertible inverse latexes, such as, for example, mixtures of alkyl polyglucosides, the hydrocarbon alkyl chains of which are decyl, dodecyl and tetradecyl chains, such as the mixture sold under the brand name Simulsol™ SL 10, dodecyl, tetradecyl and hexadecyl chains, such as the mixture sold under the name brand Simulsol™ SL 26, octyl and decyl chains, such as the mixture sold under the brand name Simulsol™ SL 8, or the undecylenyl chain, such as the mixture sold under the brand name Simulsol™ SL 11W.

However, the use of such compounds for preparing self-invertible inverse latexes has to be carried out at a temperature greater than their melting point, generally greater than 70° C., which poses problems of increase in the viscosity of the inverse latex and results in a degree of destabilization of said self-invertible inverse latex prepared. In some cases, it is carried out by prediluting said alkyl polyglycosides in water in order to have available a liquid form which can be handled at ambient temperature. This sometimes has the consequence of reducing the rate of inversion of said self-invertible inverse latexes in the polar phases to be thickened, and thus of reducing the productivity of processes for the preparation of cosmetic formulations comprising such thickening agents.

The international application published under the number WO 2009/156691 discloses the use of polyglycerol esters as inverting agents for preparing self-invertible inverse latexes, for example decaglycerol esters, such as decaglycerol monolaurate, decaglycerol oleate, decaglycerol monocaprylate or decaglycerol monomyristate. However, their use leads to self-invertible inverse latexes for which the rate of inversion in the polar phases to be thickened is too slow and even decreases when the self-invertible inverse latex is stored after its preparation for more than one month of preparation.

SUMMARY OF THE INVENTION

The inventors have thus sought to develop a novel inverting surfactant system of oil-in-water type, compatible with the environmental standards in force, being in particular devoid of alkylene oxide units, which make it possible to prepare self-invertible inverse latexes:
which can be usable easily and in particular which can be pumped at 25° C., which have a viscosity of less than or equal to 8000 mPa·s, preferably of less than or equal to 5000 mPa·s, which viscosity is measured at 25° C. using a Brookfield RVT viscometer and the No. 3 spindle at a speed of 20 revolutions/minute,
which exhibit a smooth appearance, and are devoid of grains or lumps, and
which have good inversion properties in polar phases, that is to say inducing a fast and reliable inversion speed.

A subject matter of the invention is thus a self-invertible inverse latex of a crosslinked anionic polyelectrolyte (P) comprising, per 100 mol %:
($a_1$)—of a proportion of greater than or equal to 30 mol % and less than or equal to 100 mol % of monomer units resulting from 2-methyl-2-[(1-oxo-2-propenyl)amino]-1-propanesulfonic acid in free acid or partially or totally salified form;
($a_2$)—optionally of a proportion of greater than 0 mol % and less than or equal to 70 mol % of monomer units resulting from at least one monomer chosen from the elements of the group consisting of acrylic acid, methacrylic acid, 2-(carboxyethyl)acrylic acid, itaconic acid, maleic acid and 3-methyl-3-[(1-oxo-2-propenyl)amino]butanoic acid, the carboxyl functional group of said monomers being in the free acid, partially salified or completely salified form, and/or from the elements of the group consisting of 2-hydroxyethyl acrylate, 2,3-dihydroxypropyl acrylate, 2-hydroxyethyl methacrylate, 2,3-dihydroxypropyl methacrylate, or vinylpyrrolidone;
($a_3$)—of a proportion of greater than 0 mol % and less than or equal to 1 mol % of monomer units resulting from at least one diethylenic or polyethylenic crosslinking monomer (AR);
the sum of said molar proportions of monomer units according to $a_1$), $a_2$) and $a_3$) being equal to 100 mol %;
said self-invertible inverse latex being an emulsion of water-in-oil type (W) comprising, per 100% of its weight:
a)—from 10% by weight to 90% by weight of said crosslinked anionic polyelectrolyte (P);
b)—from 5% by weight to 50% by weight of a fatty phase constituted of at least one oil (O);
c)—from 1% by weight to 50% by weight of water;
d)—from 0.5% by weight to 10% by weight of an emulsifying system of water-in-oil type ($S_1$); and
e)—from 2% by weight to 10% by weight of an emulsifying system of oil-in-water type ($S_2$);
the sum of the proportions by weight of compounds according to a), b), c), d) and e) being equal to 100% by weight;
said self-invertible inverse latex being characterized in that said emulsifying system of oil-in-water type ($S_2$) comprises, per 100% of its weight:
f)—a proportion of greater than or equal to 50% by weight and less than or equal to 100% of a composition ($C_e$) which comprises, per 100% of its weight:
$e_1$)—from 10% by weight to 60% by weight, more particularly from 15% by weight to 60% by weight and very particularly from 15% by weight to 50% of at least one compound of formula (I):

$$HO-[CH_2-CH(OH)-CH_2-O]_n-H \qquad (I)$$

in which n represents an integer greater than or equal to 1 and less than or equal to 15;
$e_2$)—from 40% by weight to 90% by weight, more particularly from 40% by weight to 85% by weight and very particularly from 50% by weight to 85% by weight of at least one compound of formula (II):

$$R_1-(C=O)-[O-CH_2-CH(OH)-CH_2]_p-OH \qquad (II),$$

in which p, which is different from or identical to n, represents an integer greater than or equal to 1 and less than or equal to 15; and in which the $R_1-(C=O)-$ group represents a saturated or unsaturated and linear or branched aliphatic radical comprising from 6 to 22 carbon atoms; and optionally
$e_3$)—up to 30% by weight, more particularly from 0% by weight to 25% by weight and very particularly from 0% by weight to 20% by weight of at least one composition ($C_{11}$) represented by the formula (III):

$$HO-[CH_2-CHOH-CH_2-O-]_q-(G)_r-H \qquad (III),$$

in which q, which is different from or identical to n, represents an integer greater than or equal to 1 and less than or equal to 3, G represents the residue of a reducing sugar and r represents a decimal number greater than or equal to 1.05 and less than or equal to 5.00;
said composition ($C_{11}$) consisting of a mixture of the compounds of formulae ($III_1$), ($III_2$), ($III_3$), ($III_4$) and ($III_5$):

$$HO-[CH_2-CHOH-CH_2-O-]_q-O-(G)_1-H \qquad (III_1),$$

$$HO-[CH_2-CHOH-CH_2-O-]_q-O-(G)_2-H \qquad (III_2),$$

$$HO-[CH_2-CHOH-CH_2-O-]_q-O-(G)_3-H \qquad (III_3),$$

$$HO-[CH_2-CHOH-CH_2-O-]_q-O-(G)_4-H \qquad (III_4),$$

$$HO-[CH_2-CHOH-CH_2-O-]_q-O-(G)_5-H \qquad (III_5),$$

in molar proportions of said compounds of formulae ($III_1$), ($III_2$), ($III_3$), ($III_4$) and ($III_5$) respectively equal to $a_1$, $a_2$, $a_3$, $a_4$ and $a_5$, such that the sum ($a_1+a_2+a_3+a_4+a_5$) is equal to 1, and that the sum ($a_1+2a_2+3a_3+4a_4+5a_5$) is equal to r;
the sum of the proportions by weight of compounds according to $e_1$), $e_2$) and $e_3$) being equal to 100% by weight.

Within the meaning of the present invention, crosslinked anionic polyelectrolyte (P) denotes, for the polymer (P), a nonlinear polyelectrolyte which is provided in the form of a three-dimensional network which is insoluble in water but which can swell in water and which then results in a chemical gel being obtained.

Within the meaning of the present invention, the term "salified" indicates that the acid functional group present in a monomer is in an anionic form associated in the salt form with a cation, in particular alkali metal salts, such as sodium or potassium cations, or such as nitrogenous base cations, such as the ammonium salt, the lysine salt or the monoethanolamine ($HOCH_2—CH_2—NH_4^+$) salt. They are preferably sodium or ammonium salts.

According to a particular aspect of the present invention, said self-invertible inverse latex as defined above comprises from 20% by weight to 90% by weight, and more particularly from 30% by weight to 90% by weight, more particularly from 30% by weight to 80% by weight, and more particularly still from 33% by weight to 80% by weight of said crosslinked anionic polyelectrolyte (P).

According to another particular aspect of the present invention, the molar proportion of monomer units resulting from 2-methyl-2-[(1-oxo-2-propenyl)amino]-1-propanesulfonic acid in free acid or partially or completely salified form present in said crosslinked anionic polyelectrolyte (P) is greater than or equal to 32 mol % and less than or equal to 100 mol %, more particularly greater than or equal to 40 mol % and less than or equal to 100 mol %.

According to a particular aspect of the present invention, the 2-methyl-2-[(1-oxo-2-propenyl)amino]-1-propanesulfonic acid is in the sodium or ammonium salt form.

According to another particular aspect of the present invention, said crosslinked anionic polyelectrolyte (P) results from the polymerization, per 100 mol %:

($a_1$)—of a proportion of greater than or equal to 32 mol % and less than 100 mol %, more particularly of greater than or equal to 40 mol % and less than or equal to 100 mol %, of monomer units resulting from a monomer possessing a strong acid functional group, which is partially salified or completely salified, more particularly of a sodium salt or an ammonium salt of 2-methyl-2-[(1-oxo-2-propenyl)amino]-1-propanesulfonic acid; and ($a_2$)—of a proportion of greater than 0 mol % and less than or equal to 68 mol %, more particularly of greater than 0 mol % and less than or equal to 60 mol %, of monomer units resulting from at least one monomer chosen from the elements of the group consisting of acrylic acid, methacrylic acid, 2-(carboxyethyl)acrylic acid, itaconic acid, maleic acid and 3-methyl-3-[(1-oxo-2-propenyl)amino]butanoic acid, the carboxyl functional group of said monomers being in the acid, partially salified or completely salified form, and/or from the elements of the group consisting of 2-hydroxyethyl acrylate, 2,3-dihydroxypropyl acrylate, 2-hydroxyethyl methacrylate, 2,3-dihydroxypropyl methacrylate and vinylpyrrolidone; and ($a_3$)—of a proportion of greater than 0 mol % and less than or equal to 1 mol % of monomer units resulting from at least one diethylenic or polyethylenic crosslinking monomer (AR); it being understood that the sum of the molar proportions of the monomer units ($a_1$), ($a_2$) and ($a_3$) is equal to 100%.

At least one diethylenic or polyethylenic crosslinking monomer (AR) denotes, in the definition of said crosslinked anionic polyelectrolyte (P), in particular a monomer chosen from methylenebis(acrylamide), ethylene glycol dimethacrylate, diethylene glycol diacrylate, ethylene glycol diacrylate, diallylurea, triallylamine, trimethylolpropane triacrylate or methylenebis(acrylamide) or a mixture of these compounds, diallyoxyacetic acid or one of its salts, such as sodium diallyloxyacetate, or a mixture of these compounds; and more particularly a monomer chosen from ethylene glycol dimethacrylate, triallylamine, trimethylolpropane triacrylate or methylenebis(acrylamide) or a mixture of these compounds.

According to another particular aspect, said crosslinking monomer (AR) is used in a molar proportion of less than or equal to 0.5%, more particularly of less than or equal to 0.25% and very particularly of less than or equal to 0.1%; it is more particularly greater than or equal to 0.005 mol %.

According to another particular aspect of the present invention, said crosslinked anionic polyelectrolyte (P) is a homopolymer of 2-methyl-2-[(1-oxo-2-propenyl)amino]-1-propanesulfonic acid partially or completely salified in the sodium salt or ammonium salt form, crosslinked by triallylamine and/or methylenebis(acrylamide); a copolymer of 2-methyl-2-[(1-oxo-2-propenyl)amino]-1-propanesulfonic acid and of acrylic acid which are partially or completely salified in the sodium salt or ammonium salt form, crosslinked by triallylamine and/or methylenebis(acrylamide); a copolymer of 2-methyl-2-[(1-oxo-2-propenyl)amino]-1-propanesulfonic acid (γ) partially or completely salified in the sodium salt form and of acrylic acid (δ) partially or completely salified in the sodium salt form in a molar ratio (γ)/(δ) of greater than or equal to 30/70 and less than or equal to 90/10, crosslinked by triallylamine and/or methylenebis(acrylamide); or a copolymer of 2-methyl-2-[(1-oxo-2-propenyl)amino]-1-propanesulfonic acid (γ) partially or completely salified in the sodium salt form and of acrylic acid (δ) partially or completely salified in the sodium salt form in a molar ratio (γ)/(δ) of greater than or equal to 40/60 and less than or equal to 90/10, crosslinked by triallylamine and/or methylenebis(acrylamide).

Oil (O) denotes, in the definition of said self-invertible inverse latex, in particular:

linear alkanes comprising from 11 to 19 carbon atoms;

branched alkanes comprising from 7 to 40 carbon atoms, such as isododecane, isopentadecane, isohexadecane, isoheptadecane, isooctadecane, isononadecane or isoeicosane, or mixtures of some of them, such as those mentioned below and identified by their INCI name: $C_{7-8}$ isoparaffin, $C_{8-9}$ isoparaffin, $C_{9-11}$ isoparaffin, $C_{9-12}$ isoparaffin, $C_{9-13}$ isoparaffin, $C_{9-14}$ isoparaffin, $C_{9-16}$ isoparaffin, $C_{10-11}$ isoparaffin, $C_{10-12}$ isoparaffin, $C_{10-13}$ isoparaffin, $C_{11-12}$ isoparaffin, $C_{11-13}$ isoparaffin, $C_{11-14}$ isoparaffin, $C_{12-14}$ isoparaffin, $C_{12-20}$ isoparaffin, $C_{13-14}$ isoparaffin, $C_{13-16}$ isoparaffin;

cycloalkanes optionally substituted by one or more linear or branched alkyl radicals;

white mineral oils, such as those sold under the following names: Marcol™ 52, Marcol™ 82, Drakeol™ 6VR, Eolane™ 130 or Eolane™ 150;

hemisqualane (or 2,6,10-trimethyldodecane; CAS number: 3891-98-3), squalane (or 2,6,10,15,19,23-hexamethyltetracosane), hydrogenated polyisobutene or hydrogenated polydecene;

mixtures of alkanes comprising from 15 to 19 carbon atoms, said alkanes being linear alkanes, branched alkanes and cycloalkanes, and more particularly the mixture ($M_1$) which comprises, per 100% of its weight, a proportion by weight of branched alkanes of greater than or equal to 90% and less than or equal to 100%; a proportion by weight of linear alkanes of greater than or equal to 0% and less than or equal to 9%, and more particularly less than 5%, and a proportion by weight of cycloalkanes of greater than or equal to 0% and less than or equal to 1%, for example the mixtures sold under the name Emogreen™ L15 or Emogreen™ L19;

the fatty alcohol ethers of formula (IV):

$$Z_1—O—Z_2 \qquad (IV),$$

in which $Z_1$ and $Z_2$, which are identical or different, represent a linear or branched alkyl radical comprising from 5 to 18 carbon atoms, for example dioctyl ether, didecyl ether, didodecyl ether, dodecyl octyl ether, dihexadecyl ether, 1,3-dimethylbutyl tetradecyl ether, 1,3-dimethylbutyl hexadecyl ether, bis(1,3-dimethylbutyl) ether or dihexyl ether;

monoesters of fatty acids and of alcohols of formula (V):

in which $R'_1$—(C=O) represents a saturated or unsaturated and linear or branched acyl radical comprising from 8 to 24 carbon atoms and $R'_2$ represents, independently of $R'_1$, a saturated or unsaturated and linear or branched hydrocarbon chain comprising from 1 to 24 carbon atoms, for example methyl laurate, ethyl laurate, propyl laurate, isopropyl laurate, butyl laurate, 2-butyl laurate, hexyl laurate, methyl cocoate, ethyl cocoate, propyl cocoate, isopropyl cocoate, butyl cocoate, 2-butyl cocoate, hexyl cocoate, methyl myristate, ethyl myristate, propyl myristate, isopropyl myristate, butyl myristate, 2-butyl myristate, hexyl myristate, octyl myristate, methyl palmitate, ethyl palmitate, propyl palmitate, isopropyl palmitate, butyl palmitate, 2-butyl palmitate, hexyl palmitate, octyl palmitate, methyl oleate, ethyl oleate, propyl oleate, isopropyl oleate, butyl oleate, 2-butyl oleate, hexyl oleate, octyl oleate, methyl stearate, ethyl stearate, propyl stearate, isopropyl stearate, butyl stearate, 2-butyl stearate, hexyl stearate, octyl stearate, methyl isostearate, ethyl isostearate, propyl isostearate, isopropyl isostearate, butyl isostearate, 2-butyl isostearate, hexyl isostearate or isostearyl isostearate;

diesters of fatty acids and of glycerol of formula (VI) and of formula (VII):

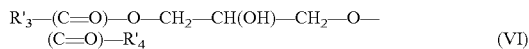

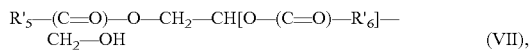

in which formulae (VI) and (VII) $R'_3$—(C=O), $R'_4$—(C=O), $R'_5$—(C=O) and $R'_6$—(C=O), which are identical or different, represent a saturated or unsaturated and linear or branched acyl group comprising from 8 to 24 carbon atoms;

triesters of fatty acids and of glycerol of formula (VIII):

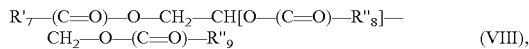

in which $R'_7$—(C=O), $R'_8$—(C=O) and $R'_9$—(C=O), which are identical or different, represent a saturated or unsaturated and linear or branched acyl group comprising from 8 to 24 carbon atoms.

According to another particular aspect of the present invention, said oil (O) is chosen from undecane, tridecane, isododecane or isohexadecane, mixtures of alkanes and isoalkanes and cycloalkanes, such as the mixture ($M_1$) as defined above and the mixtures sold under the name Emogreen™ L15, Emogreen™ L19, Emosmart™ L15, Emosmart™ L19, Emosmart™ V21, Isopar™ L or Isopar™ M; the white mineral oils sold under the name Marcol™ 52, Marcol™ 82, Drakeol™ 6VR, Eolane™ 130 or Eolane™ 150; hemisqualane, squalane, hydrogenated polyisobutene or hydrogenated polydecene; dioctyl ether or didecyl ether; isopropyl myristate, hexyl palmitate, octyl palmitate, isostearyl isostearate, octanoyl/decanoyl triglyceride, hexadecanoyl/octadecanoyl triglyceride or the triglycerides resulting from rapeseed oil, sunflower oil, linseed oil or palm oil.

In said self-invertible inverse latex which is a subject matter of the present invention, the emulsifying system ($S_1$) of water-in-oil type consists either of a single emulsifying surfactant or of a mixture of emulsifying surfactants, provided that said resulting emulsifying system ($S_1$) has a sufficiently low HLB value to bring about the formation of emulsions of water-in-oil type.

There are, as emulsifying surfactant of water-in-oil type, for example, esters of anhydrohexitol and of linear or branched and saturated or unsaturated aliphatic carboxylic acids comprising from 12 to 22 carbon atoms, optionally substituted with one or more hydroxyl groups, and more particularly esters of anhydrohexitols chosen from anhydrosorbitols and anhydromannitols and of linear or branched and saturated or unsaturated aliphatic carboxylic acids comprising from 12 to 22 carbon atoms, optionally substituted with one or more hydroxyl groups.

According to another particular aspect of the present invention, said emulsifying system ($S_1$) of water-in-oil type is chosen from the elements of the group consisting of sorbitan laurate, for example that sold under the name Montane™ 20, sorbitan palmitate, for example that sold under the name Montane™ 40, sorbitan stearate, for example that sold under the name Montane™ 60, sorbitan oleate, for example that sold under the name Montane™ 80, sorbitan sesquioleate, for example that sold under the name Montane™ 85, sorbitan trioleate, for example that sold under the name Montane™ 83, sorbitan isolaurate, sorbitan isostearate, for example that sold under the name Montane™ 70, mannitan laurate, mannitan oleate and a mixture of these esters; polyesters with a molecular weight of between 1000 and 3000 and resulting from the condensation between a polyisobutenyl succinic acid or its anhydride, such as Hypermer™ 2296, or the mixture sold under the brand name Simaline™ IE 501 A, the polyhydroxystearates of polyglycols of formula (IX):

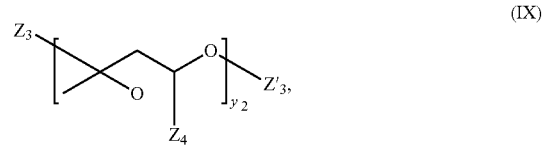

in which formula (IX) $y_2$ represents an integer greater than or equal to 2 and less than or equal to 50, $Z_4$ represents a hydrogen atom, a methyl radical or an ethyl radical, and $Z_3$ represents a radical of formula (X):

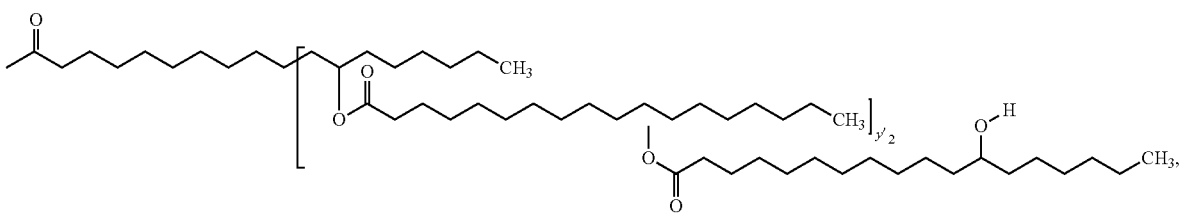

in which formula (X) $y'_2$ represents an integer greater than or equal to 0 and less than or equal to 10, more particularly greater than or equal to 1 and less than or equal to 10, and $Z'_3$ represents a radical of formula (X) as defined above, with $Z'_3$ being identical to or different from $Z_3$, or a hydrogen atom.

There is, as example of emulsifying surfactant of water-in-oil type of formula (IX) which can be used to prepare the emulsifying system ($S_1$), PEG-30 dipolyhydroxystearate sold under the name Simaline™ WO, or else the mixtures comprising PEG-30 dipolyhydroxystearate and sold under the names Simaline™ IE 201 A and Simaline™ IE 201 B, or also the mixture comprising trimethylolpropane-30 tripolyhydroxystearate sold under the name Simaline™ IE 301 B.

In said self-invertible inverse latex which is a subject matter of the present invention, the emulsifying system ($S_2$) of oil-in-water type consists either of the composition ($C_e$) alone or of a mixture of said composition ($C_e$) with one or more other emulsifying surfactants, provided that said resulting emulsifying system ($S_2$) has a sufficiently high HLB value to bring about the formation of emulsions of oil-in-water type.

According to another more particular aspect of the present invention, said self-invertible inverse latex as defined above is characterized in that, in the formula (I), n represents an integer greater than or equal to 1 and less than or equal to 10, and in that, in the formula (II), p, which is identical to or different from n, represents an integer greater than or equal to 1 and less than or equal to 10, and the $R_1$—(C=O)— group is chosen from octanoyl, decanoyl, ω-undecylenoyl, dodecanoyl, tetradecanoyl, hexadecanoyl, octadecanoyl, 9-octadecenoyl or 9,12-octadecadienoyl radicals.

According to another even more particular aspect of the present invention, in said formulae (I) and (II) as defined above, n is equal to 10, p is equal to 10 and the $R_1$—(C=O)— group is the dodecanoyl radical; n is equal to 6, p is equal to 10 and the $R_1$—(C=O)— group is the dodecanoyl radical; n is equal to 6, p is equal to 6 and the $R_1$—(C=O)— group is the dodecanoyl radical or n is equal to 1, p is equal to 10 and the $R_1$—(C=O)— group is the dodecanoyl radical.

According to another more particular aspect of the present invention, said self-invertible inverse latex as defined above is characterized in that, in said emulsifying system of oil-in-water type ($S_2$), said composition ($C_e$) as defined above consists of, per 100% of its weight:
- $e_1$)—from 10% by weight to 60% by weight of at least one compound of formula (I) as defined above and
- $e_2$)—from 40% by weight to 90% by weight of at least one compound of formula (II) as defined above.

Reducing sugar denotes, in the formula (III) as defined above, the saccharide derivatives which do not exhibit, in their structures, a glycoside bond established between an anomeric carbon and the oxygen of an acetal group as defined in the reference publication: "Biochemistry", Daniel Voet/Judith G. Voet, p. 250, John Wiley & Sons, 1990. The oligomeric structure $(G)_x$ can exist in all forms of isomerisms, whether it is optical isomerism, geometrical isomerism or positional isomerism; it can also represent a mixture of isomers.

According to another more particular aspect of the present invention, in the composition ($C_e$) as defined above, G represents, in the formula (III) as defined above, the residue of a reducing sugar chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose. Said residue G represents more particularly still, in the formula (III) as defined above, a reducing sugar chosen from the residues of glucose, xylose and arabinose.

The formula (III):

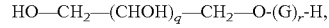

representing the composition ($C_{11}$), means that this composition ($C_1$) is composed essentially of a mixture of compounds represented by the formulae ($III_1$), ($III_2$), ($III_3$), ($III_4$) and ($III_5$):

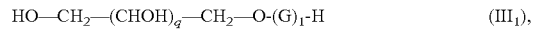

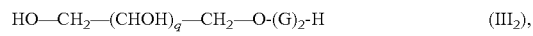

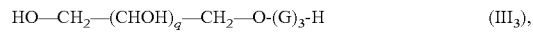

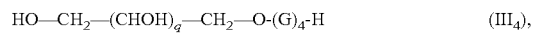

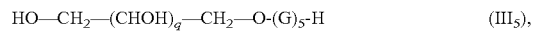

in the respective molar proportions $a_1$, $a_2$, $a_3$, $a_4$ and $a_5$, such that:
the sum $a_1+a_2+a_3+a_4+a_5$ is equal to 1, and that
the sum $a_1+2a_2+3a_3+4a_4+5a_5$ is equal to r.

In the preceding definition, essentially indicates that the presence of one or more compounds of formula ($III_w$) with w greater than 5 is not excluded within the composition ($C_{11}$) but that, if it is present, then it is present in minimal proportions which do not result in any substantial modification to the properties of said composition ($C_{11}$). In the formula (III) as defined above, the HO—$CH_2$—$(CHOH)_q$—$CH_2$—O— group is bonded to $(G)_r$ via the anomeric carbon of the saccharide residue, so as to form an acetal functional group.

According to a more particular aspect of the present invention, in the formula (III) representing the composition ($C_{11}$) as defined above, r represents a decimal number greater than or equal to 1.05 and less than or equal to 3, more particularly greater than or equal to 1.15 and less than or equal to 2.5.

According to a more particular aspect of the present invention, said self-invertible inverse latex as defined above is characterized in that, in the formula (III) as defined above, q is equal to 1, G represents the residue of glucose and r represents a decimal number greater than or equal to 1.05 and less than or equal to 2.5.

According to another particular aspect of the present invention, said self-invertible inverse latex as defined above is characterized in that, in said emulsifying system of oil-in-water type ($S_2$), said composition ($C_e$) as defined above consists of, per 100% of its weight:
- $e_1$)—from 5% by weight to 15% by weight of at least one compound of formula (I) as defined above,
- $e_2$)—from 60% by weight to 80% by weight of at least one compound of formula (II) as defined above, and
- $e_3$)—from 5% to 15% by weight of at least one composition ($C_{11}$) represented by the formula (III) as defined above.

According to another particular aspect of the present invention, said emulsifying system ($S_2$) of oil-in-water type comprises, per 100% of its weight, at least 75% by weight of said composition ($C_e$) as defined above.

According to a very particular aspect, said inverse latex as defined above is characterized in that said emulsifying system of oil-in-water type ($S_2$) is said composition ($C_e$) as defined above.

Said self-invertible inverse latex which is a subject matter of the present invention is prepared by the implementation of an "inverse emulsion polymerization" process, well known to a person skilled in the art, and which comprises the following stages:
- a stage a) of preparation of an aqueous phase comprising water, water-soluble monomers and optionally the crosslinking monomer (AR), and also commonly used additives, such as, for example, sequestering agents, such as ethylenediaminetetraacetic acid (EDTA) in its sodium salt form, or the pentasodium salt of diethylenetriaminepentaacetic acid (sold under the brand name Versenex™ 80);
- a stage b) of mixing the oily phase (O) with the emulsifying system of water-in-oil type ($S_1$);
- a stage c) of mixing the aqueous phase and the oily phase, prepared during the preceding stages, and of emulsification using a stirrer of rotor-stator type;
- a stage d) of rendering inert with nitrogen;
- a stage e) of initiation of the polymerization reaction by introduction, into the emulsion formed in c), of a free radical initiator and optionally of a coinitiator; then the reaction is allowed to take place,
- a stage f) of introduction of the emulsifying system ($S_2$) of oil-in-water type as defined above at a temperature of less than or equal to 50° C.

According to a particular aspect of the process as defined above, the polymerization reaction of stage e) is initiated by a redox pair which generates hydrogen sulfite ($HSO_3^-$) ions, such as the cumene hydroperoxide/sodium metabisulfite ($Na_2S_2O_5$) pair or the cumene hydroperoxide/thionyl chloride ($SOCl_2$) pair, at a temperature of less than or equal to 10° C., accompanied, if desired, by a polymerization coinitiator, such as, for example, azobis(isobutyronitrile), and is then carried out either quasi-adiabatically, up to a temperature of greater than or equal to 50° C., or by controlling the temperature.

According to another particular aspect of the process as defined above, the reaction medium resulting from stage e) is concentrated by distillation, before carrying out stage f).

According to another particular aspect of the process as defined above, the reaction medium resulting from stage e) or from stage f) undergoes a stage of drying by atomization in a suitable installation.

According to another particular aspect of the process as defined above, the aqueous phase prepared in stage a) can comprise chain-reducing agents, intended to reduce the length of the polymer chains formed and to increase the degree of branching on the polymer, so as to modify the rheological properties.

The chain-reducing agents suitable for the process as defined above include methanol, isopropanol, butylene glycol, 2-mercaptoethanol, thioglycolic acid, formic acid or its salts.

Another subject matter of the invention is a composition ($C_e$) which comprises, per 100% of its weight:
- $e_1$)—from 10% by weight to 60% by weight, more particularly from 15% by weight to 60% by weight and more particularly still from 15% by weight to 50% by weight of at least one compound of formula (I):

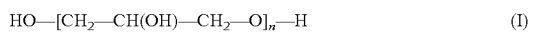

in which n represents an integer greater than or equal to 1 and less than or equal to 15;
- $e_2$)—from 40% by weight to 90% by weight, more particularly from 40% by weight to 85% by weight and more particularly still from 50% by weight to 85% by weight of at least one compound of formula (II):

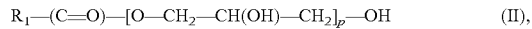

in which p, which is different from or identical to n, represents an integer greater than or equal to 1 and less than or equal to 15; and the $R_1$—(C=O)— group represents a saturated or unsaturated and linear or branched aliphatic radical comprising from 6 to 22 carbon atoms; and optionally
- $e_3$)—up to 30% by weight 0% by weight to 30% by weight, more particularly from 0% by weight to 25% by weight and more particularly from 0% by weight to 20% by weight of at least one composition ($C_{11}$) represented by the formula (III):

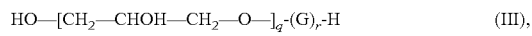

in which formula (III) q, which is different from or identical to n, represents an integer greater than or equal to 1 and less than or equal to 3, G represents the residue of a reducing sugar and r represents a decimal number greater than or equal to 1.05 and less than or equal to 5.00, said composition ($C_{11}$) consisting of a mixture of the compounds of formulae ($III_1$), ($III_2$), ($III_3$), ($III_4$) and ($III_5$):

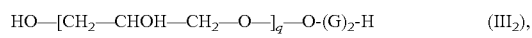

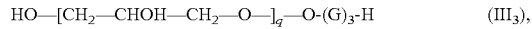

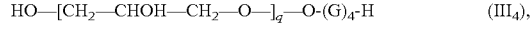

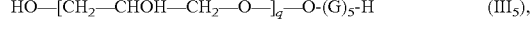

in molar proportions of said compounds of formulae ($III_1$), ($III_2$), ($III_3$), ($III_4$) and ($III_5$) respectively equal to $a_1$, $a_2$, $a_3$, $a_4$ and $a_5$, such that the sum $a_1+a_2+a_3+a_4+a_5$ is equal to 1, and that the sum $a_1+2a_2+3a_3+4a_4+5a_5$ is equal to r;

the sum of the proportions by weight of compounds according to $e_1$), $e_2$) and $e_3$) being equal to 100% by weight.

According to a particular aspect, the composition ($C_e$) as defined above is characterized in that, in the formula (I), n represents an integer greater than or equal to 1 and less than or equal to 10 and, in formula (II), p, which is different from n, represents an integer greater than or equal to 1 and less than or equal to 10.

According to this particular aspect, the composition ($C_e$) as defined above is more particularly characterized in that, in the formula (I) as defined above, n is equal to 1 or to 6 and, in the formula (II), p is equal to 6 or to 10.

According to this particular aspect, the composition ($C_e$) as defined above is also characterized in that, in the formulae (I) and (II) as defined above, n and p are identical and each represent an integer greater than or equal to 1 and less than or equal to 10 and in particular greater than or equal to 4 and less than or equal to 8.

According to this particular aspect, the composition ($C_e$) as defined above is more particularly characterized in that, in the formulae (I) and (II) as defined, n and p are equal to 6.

According to another particular aspect of the present invention, in the formula (II) as defined above, the $R_1$—(C=O)— group is chosen from the elements of the group consisting of the octanoyl, decanoyl, ω-undecylenoyl, dodecanoyl, tetradecanoyl, hexadecanoyl, octadecanoyl, 9-octadecenoyl and 9,12-octadecadienoyl radicals; it is more particularly the dodecanoyl radical.

A subject matter of the invention is also particularly the composition ($C_e$) as defined above, characterized in that it consists of, per 100% of its weight:

$e_1$)—from 10% by weight to 60% by weight of at least one compound of formula (I) as defined above and $e_2$)—from 40% by weight to 90% by weight of at least one compound of formula (II) as defined above.

A subject matter of the invention is also particularly the composition ($C_e$) as defined above, characterized in that, in the formula (III) as defined above, q is equal to 1, G represents the residue of glucose and r represents a decimal number greater than or equal to 1.05 and less than or equal to 2.5.

According to another particular aspect of the present invention, the composition ($C_e$) as defined above is characterized in that it consists of, per 100% of its weight:

$e_1$)—from 5% by weight to 15% by weight of at least one compound of formula (I) as defined above, $e_2$)—from 60% by weight to 80% by weight of at least one compound of formula (II) as defined above, and $e_3$)—from 5% to 15% by weight of at least one composition ($C_{11}$) represented by the formula (III) as defined above.

Reducing sugar denotes, in the formula (III), the saccharide derivatives as defined above and G represents, in the formula (III) as defined above, the residue of a reducing sugar chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose, and more particularly from the residues of glucose, xylose and arabinose.

The formula (III) representing the composition ($C_{11}$) consists of a mixture of compounds represented by the formulae ($III_1$), ($III_2$), ($III_3$), ($III_4$) and ($III_5$) as defined above. According to a more particular aspect of the present invention, in the formula (III) representing the composition ($C_{11}$) as defined above, r represents a decimal number greater than or equal to 1.05 and less than or equal to 3, more particularly greater than or equal to 1.15 and less than or equal to 2.5.

According to a more particular aspect, a subject matter of the invention is a composition ($C_e$) as defined above, for which, in the formula (III), q is equal to 1, G represents the residue of glucose and r represents a decimal number greater than or equal to 1.05 and less than or equal to 2.5.

According to another particular aspect, a subject matter of the invention is a composition ($C_e$) as defined above, for which, in the formula (I), n represents an integer greater than or equal to 1 and less than or equal to 10, in the formula (II), p, which is identical to or different from n, represents an integer greater than or equal to 1 and less than or equal to 10 and the $R_1$—(C=O)— group is chosen from the octanoyl, decanoyl, ω-undecylenoyl, dodecanoyl, tetradecanoyl, hexadecanoyl, octadecanoyl, 9-octadecenoyl or 9,12-octadecadienoyl radicals, and, in the formula (III), q is equal to 1, G represents the residue of glucose and r represents a decimal number greater than or equal to 1.05 and less than or equal to 2.5.

According to a very particular aspect, a subject matter of the invention is a composition ($C_e$) as defined above, for which, in the formula (I), n is equal to 1, in the formula (II), p is equal to 10 and the $R_1$—(C=O)— group is the dodecanoyl radical and, in the formula (III), q is equal to 1, G represents the residue of glucose and r represents a decimal number greater than or equal to 1.05 and less than or equal to 2.5.

The composition ($C_{11}$) optionally comprised in the composition ($C_e$) is prepared according to a process comprising the following stages:

a stage A) of reaction, in the desired proportions, of a reducing sugar of formula (XI) or a mixture of reducing sugars of formula (XI):

HO-G-H (XI)

in which G represents the residue of a reducing sugar, with a molar excess of a compound of formula (XII) or of a mixture of compounds of formula (XII):

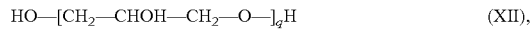

HO—[CH$_2$—CHOH—CH$_2$—O—]$_q$H (XII), for which formula (XII) q is as defined above for the formula (III), in order to form a mixture of compounds of formula (III) as defined above and an excess of said compound of formula (XII).

Stage A) of the process as defined above can be supplemented, if necessary or if desired, by subsequent operations of neutralization, for example with sodium hydroxide or potassium hydroxide, and/or of filtration, and/or of decoloration, and/or of removal of the residual polyol, for example by selective extraction by means of a suitable solvent medium.

Stage A) is generally carried out in a reactor in the presence of an acidic catalytic system, by controlling the stoichiometric ratio between the two reagents, and more particularly by introducing a molar excess of the mixture of alcohols of formula (II), with mechanical stirring under predetermined temperature and partial vacuum conditions, for example at a temperature of between 70° C. and 130° C. and under a partial vacuum of between 300 mbar (3.10$^4$ Pa) and 20 mbar (2.10$^3$ Pa). Acidic catalytic system denotes strong acids, such as sulfuric acid, hydrochloric acid, phosphoric acid, nitric acid, hypophosphorous acid, methanesulfonic acid, para-toluenesulfonic acid or trifluoromethanesulfonic acid, or ion-exchange resins.

Another subject matter of the invention is the use of said self-invertible inverse latex as defined above as thickening and/or emulsifying and/or stabilizing agent for a topical cosmetic or pharmaceutical composition.

According to another particular aspect, said use consists in stabilizing an emulsion of oil-in-water type or of water-in-oil type, conferring a homogeneous appearance on said emulsion during storage under various conditions and more particularly at 25° C. for a time at least equal to one month, and more particularly at 4° C. for a time at least equal to one month, and more particularly at 45° C. for a time at least equal to one month.

According to another particular aspect, said use consists in stabilizing solid particles in topical cosmetic, dermopharmaceutical or pharmaceutical compositions. These solid particles to be suspended can assume various regular or irregular geometries, and can be provided in the form of beads, balls, rods, flakes, strips or polyhedra. These solid particles are characterized by a mean apparent diameter of between 1 micrometer and 5 millimeters, more particularly between 10 micrometers and 1 millimeter.

The solid particles which can be suspended and stabilized by the self-invertible inverse latex as defined above in topical cosmetic, dermopharmaceutical or pharmaceutical compositions include micas, iron oxide, titanium oxide, zinc oxide, aluminum oxide, talc, silica, kaolin, clays, boron nitride, calcium carbonate, magnesium carbonate, magnesium hydrogencarbonate, inorganic colored pigments, polyamides, such as Nylon-6, polyethylenes, polypropylenes, polystyrenes, polyesters, acrylic or methacrylic polymers, such as polymethyl methacrylates, polytetrafluoroethylene, crystalline or microcrystalline waxes, porous spheres, selenium sulfide, zinc pyrithione, starches, alginates, plant fibers, loofah particles and sponge particles.

Another subject matter of the invention is a topical cosmetic composition (F) or a topical pharmaceutical composition (G), characterized in that it comprises, as thickening agent, per 100% of its total weight, between 0.1% and 10% by weight of said self-invertible inverse latex as defined above.

The expression "topical" used in the definitions of said compositions (F) and (G) means that they are employed by application to the skin, the hair, the scalp or the mucous membranes, whether it is a direct application, in the case of a cosmetic, dermocosmetic, dermopharmaceutical or pharmaceutical preparation, or an indirect application, for example in the case of a body care product in the form of a textile or paper wipe or of sanitary products intended to be in contact with the skin or the mucous membranes.

Said compositions (F) and (G) are generally provided in the form of an aqueous or aqueous/alcoholic or aqueous/glycolic solution, in the form of a suspension, of an emulsion, of a microemulsion or of a nanoemulsion, whether they are of water-in-oil, oil-in-water, water-in-oil-in-water or oil-in-water-in-oil type.

Said compositions (F) and (G) can be packaged in a bottle, in a device of "pump-action spray" type, in pressurized form in an aerosol device, in a device equipped with a perforated wall, such as a grill, or in a device equipped with a ball applicator (known as a "roll-on").

In general, said compositions (F) and (G) also comprise excipients and/or active principles habitually employed in the field of formulations for topical use, in particular cosmetic, dermocosmetic, pharmaceutical or dermopharmaceutical formulations, such as thickening and/or gelling surfactants, stabilizers, film-forming compounds, hydrotropic agents, plasticizing agents, emulsifying and coemulsifying agents, opacifying agents, pearlescent agents, superfatting agents, sequestering agents, chelating agents, antioxidants, fragrances, preservatives, conditioning agents, whitening agents intended for bleaching body hairs and the skin, active principles intended to contribute a treating action with regard to the skin or hair, sunscreens, pigments or inorganic fillers, particles providing a visual effect or intended for the encapsulation of active principles, exfoliating particles or texturing agents.

Examples of foaming and/or detergent surfactants which can be combined with said self-invertible inverse latex as defined above in said compositions (F) and (G) include anionic, cationic, amphoteric or nonionic foaming and/or detergent surfactants.

Examples of anionic foaming and/or detergent surfactants which can be combined with said self-invertible inverse latex as defined above in said compositions (F) and (G) include alkali metal, alkaline earth metal, ammonium, amine or aminoalcohol salts of alkyl ether sulfates, of alkyl sulfates, of alkylamido ether sulfates, of alkylaryl polyether sulfates, of monoglyceride sulfates, of α-olefinsulfonates, of paraffinsulfonates, of alkyl phosphates, of alkyl ether phosphates, of alkylsulfonates, of alkylamidesulfonates, of alkylarylsulfonates, of alkylcarboxylates, of alkyl sulfosuccinates, of alkyl ether sulfosuccinates, of alkylamide sulfosuccinates, of alkyl sulfoacetates, of alkylsarcosinates, of acylisethionates, of N-acyltaurates, of acyl lactylates, of N-acylated derivatives of amino acids, of N-acylated derivatives of peptides, of N-acylated derivatives of proteins or of N-acylated derivatives of fatty acids.

The foaming and/or detergent amphoteric surfactants which can be combined with said self-invertible inverse latex as defined above in said compositions (F) and (G) include alkyl betaines, alkyl amido betaines, sultaines, alkyl amidoalkyl sulfobetaines, imidazoline derivatives, phosphobetaines, amphopolyacetates and amphopropionates.

The foaming and/or detergent cationic surfactants which can be combined with said self-invertible inverse latex as defined above in said compositions (F) and (G) particularly include quaternary ammonium derivatives.

The foaming and/or detergent nonionic surfactants which can be combined with said self-invertible inverse latex as defined above in said compositions (F) and (G) more particularly include alkyl polyglycosides comprising a linear or branched and saturated or unsaturated aliphatic radical and comprising from 8 to 16 carbon atoms, such as octyl polyglucoside, decyl polyglucoside, undecylenyl polyglucoside, dodecyl polyglucoside, tetradecyl polyglucoside, hexadecyl polyglucoside or 1,12-dodecanediyl polyglucoside; ethoxylated hydrogenated castor oil derivatives, such as the product sold under the INCI name "PEG-40 hydrogenated castor oil"; polysorbates, such as Polysorbate 20, Polysorbate 40, Polysorbate 60, Polysorbate 70, Polysorbate 80 or Polysorbate 85; coconut amides; or N-alkylamines.

Examples of thickening and/or gelling surfactants which can be combined with said self-invertible inverse latex as defined above in said compositions (F) and (G) include optionally alkoxylated alkyl polyglycoside fatty esters, such as ethoxylated methyl polyglucoside esters, for example the PEG 120 methyl glucose trioleate and the PEG 120 methyl glucose dioleate sold respectively under the names Glucamate™ LT and Glucamate™ DOE120; alkoxylated fatty esters, such as the PEG 150 pentaerythrityl tetrastearate sold under the name Crothix™ DS53 or the PEG 55 propylene glycol oleate sold under the name Antil™ 141; fatty-chain polyalkylene glycol carbamates, such as the PPG-14 laureth isophoryl dicarbamate sold under the name Elfacos™ T211 or the PPG-14 palmeth-60 hexyl dicarbamate sold under the name Elfacos™ GT2125.

Examples of thickening and/or gelling agents which can be combined with said self-invertible inverse latex as defined above in said compositions (F) and (G) include copolymers of AMPS and of alkyl acrylates, the carbon chain of which comprises between 4 and 30 carbon atoms and more particularly between 10 and 30 carbon atoms, linear, branched or crosslinked terpolymers of at least one monomer carrying a free, partially salified or completely salified strong acid functional group with at least one neutral monomer and at least one monomer of formula (XIII):

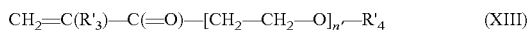

$$CH_2=C(R'_3)-C(=O)-[CH_2-CH_2-O]_{n'}-R'_4 \quad (XIII)$$

in which $R'_3$ represents a hydrogen atom or a methyl radical, $R'_4$ represents a linear or branched alkyl radical comprising from 8 to 30 carbon atoms and n' represents a number greater than or equal to 1 and less than or equal to 50.

Examples of thickening and/or gelling agents which can be combined with said self-invertible inverse latex as defined above in said compositions (F) and (G) include polysaccharides consisting solely of monosaccharides, such as glucans or glucose homopolymers, glucomannoglucans, xyloglycans, galactomannans, the degree of substitution (DS) of the D-galactose units on the main D-mannose chain of which is between 0 and 1 and more particularly between 1 and 0.25, such as galactomannans originating from cassia gum (DS=⅕), locust bean gum (DS=¼), tara gum (DS=⅓), guar gum (DS=½) or fenugreek gum (DS=1).

Examples of thickening and/or gelling agents which can be combined with said self-invertible inverse latex as defined above in said compositions (F) and (G) include polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, gum arabic exudates and karaya gum exudates, or glucosaminoglycans.

Examples of thickening and/or gelling agents which can be combined with said self-invertible inverse latex as defined above in said compositions (F) and (G) include cellulose, cellulose derivatives, such as methyl cellulose, ethyl cellulose or hydroxypropyl cellulose, silicates, starch, hydrophilic starch derivatives or polyurethanes.

Examples of stabilizing agents which can be combined with said self-invertible inverse latex as defined above in said compositions (F) and (G) include monocrystalline waxes and more particularly ozokerite, inorganic salts, such as sodium chloride or magnesium chloride, or silicone polymers, such as polysiloxane polyalkyl polyether copolymers.

Examples of solvents which can be combined with said self-invertible inverse latex as defined above in said compositions (F) and (G) include water, organic solvents, such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols, such as ethanol, isopropanol or butanol, or mixtures of water and of said organic solvents.

Examples of thermal or mineral waters which can be combined with said self-invertible inverse latex as defined above in said compositions (F) and (G) include thermal or mineral waters having a mineralization of at least 300 mg/l, in particular Avene water, Vittel water, Vichy basin water, Uriage water, La Roche-Posay water, La Bourboule water, Enghien-les-Bains water, Saint-Gervais-les-Bains water, Néris-les-Bains water, Allevard-les-Bains water, Digne water, Maizières water, Neyrac-les-Bains water, Lons-les-Saunier water, Rochefort water, Saint Christau water, Les Fumades water and Tercis-les-Bains water.

Examples of hydrotropic agents which can be combined with said self-invertible inverse latex as defined above in said compositions (F) and (G) include xylenesulfonates, cumenesulfonates, hexyl polyglucoside, 2-ethylhexyl polyglucoside and n-heptyl polyglucoside.

Examples of emulsifying surface-active agents which can be combined with said self-invertible inverse latex as defined above in said compositions (F) and (G) include non-ionic surfactants, anionic surfactants or cationic surfactants.

Examples of emulsifying nonionic surfactants which can be combined with said self-invertible inverse latex as defined above in said compositions (F) and (G) include esters of fatty acids and of sorbitol, such as the products sold under the names Montane™ 40, Montane™ 60, Montane™ 70, Montane™ 80 and Montane™ 85; compositions comprising glycerol stearate and stearic acid ethoxylated with between 5 mol and 150 mol of ethylene oxide, such as the composition comprising stearic acid ethoxylated with 135 mol of ethylene oxide and glycerol stearate sold under the name Simulsol™ 165; mannitan esters; ethoxylated mannitan esters; sucrose esters; methyl glucoside esters; alkyl polyglycosides including a linear or branched and saturated or unsaturated aliphatic radical and comprising from 14 to 36 carbon atoms, such as tetradecyl polyglucoside, hexadecyl polyglucoside, octadecyl polyglucoside, hexadecyl polyxyloside, octadecyl polyxyloside, eicosyl polyglucoside, dodecosyl polyglucoside, 2-octyldodecyl polyxyloside or 12-hydroxystearyl polyglucoside; compositions of linear or branched and saturated or unsaturated fatty alcohols and comprising from 14 to 36 carbon atoms and of alkyl polyglycosides such as described above, for example the compositions sold under the names Montanov™ 68, Montanov™ 14, Montanov™ 82, Montanov™ 202, Montanov™ S, Montanov™ WO18, Montanov™ L, Fluidanov™ 20X and Easynov™.

Examples of anionic surfactants which can be combined with said self-invertible inverse latex as defined above in said compositions (F) and (G) include glyceryl stearate citrate, cetearyl sulfate, soaps, such as sodium stearate or triethanolammonium stearate, and N-acylated derivatives of amino acids which are salified, for example stearoyl glutamate.

Examples of emulsifying cationic surfactants which can be be combined with said self-invertible inverse latex as defined above in said compositions (F) and (G) include amine oxides, quaternium-82 and the surfactants described in the patent application WO 96/00719 and mainly those, the fatty chain of which comprises at least 16 carbon atoms.

Examples of opacifying and/or pearlescent agents which can be combined with said self-invertible inverse latex as defined above in said compositions (F) and (G) include sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate or fatty alcohols comprising from 12 to 22 carbon atoms.

Examples of texturing agents which can be combined with said self-invertible inverse latex as defined above in said compositions (F) and (G) include N-acylated derivatives of amino acids, such as lauroyl lysine sold under the name Aminohope™ LL, starch octenylsuccinate sold under the name Dryflo™, myristyl polyglucoside sold under the name Montanov™ 14, cellulose fibers, cotton fibers, chitosan fibers, talc, sericite or mica.

Examples of deodorant agents which can be combined with said self-invertible inverse latex as defined above in said compositions (F) and (G) include alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glycerol caprate, glycerol caprylate or polyglycerol caprate; 1,2-decanediol; 1,3-propanediol; salicylic acid; sodium bicarbonate; cyclodextrins; metallic zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

Examples of oils which can be combined with said self-invertible inverse latex as defined above in said compositions (F) and (G) include mineral oils, such as liquid paraffin, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheat germ oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil, oils resulting from flowers or vegetables or ethoxylated vegetable oils; synthetic oils, such as fatty acid esters, for example butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, such as glycerol triheptanoate, alkylbenzoates, hydrogenated oils, poly($\alpha$-olefins), polyolefins, such as poly(isobutane), synthetic isoalkanes, such as isohexadecane or isododecane, or perfluorinated oils; silicone oils, such as dimethylpolysiloxanes, methylphenylpolysiloxanes, silicones modified by amines, silicones modified by fatty acids, silicones modified by alcohols, silicones modified by alcohols and fatty acids, silicones modified by polyether groups, epoxy-modified silicones, silicones modified by fluorinated groups, cyclic silicones and silicones modified by alkyl groups. In the present patent application, "oils" is understood to mean compounds and/or mixtures of compounds which are insoluble in water, existing under a liquid appearance at a temperature of 25° C.

Examples of waxes which can be combined with said self-invertible inverse latex as defined above in said compositions (F) and (G) include beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; vegetable waxes; fatty alcohols and fatty acids which are solid at ambient temperature, or glycerides which are solid at ambient temperature. In the present patent application, "waxes" is understood to mean compounds and/or mixtures of compounds which are insoluble in water, existing under a solid appearance at a temperature of greater than or equal to 45° C.

Examples of active principles which can be combined with said self-invertible inverse latex as defined above in said compositions (F) and (G) include vitamins and their derivatives, in particular their esters, such as retinol (vitamin A) and its esters (for example retinyl palmitate), ascorbic acid (vitamin C) and its esters, sugar derivatives of ascorbic acid (such as ascorbyl glucoside), tocopherol (vitamin E) and its esters (such as tocopheryl acetate), vitamin B3 or B10 (niacinamide and its derivatives); compounds showing a lightening or depigmenting action on the skin, such as ω-undecylenoyl phenylalanine sold under the name Sepiwhite™ MSH, Sepicalm™ VG, the glycerol monoester and/or the glycerol diester of ω-undecylenoyl phenylalanine, ω-undecylenoyl dipeptides, arbutin, kojic acid, hydroquinone; compounds showing a soothing action, in particular Sepicalm™ S, allantoin and bisabolol; antiinflammatory agents; compounds showing moisturizing action, such as urea, hydroxyureas, glycerol, polyglycerols, glycerol glucoside, diglycerol glucoside, polyglyceryl glucosides, xylityl glucoside; polyphenol-rich plant extracts, such as grape extracts, pine extracts, wine extracts or olive extracts; compounds showing a slimming or lipolytic action, such as caffeine or its derivatives, Adiposlim™, Adipoless™, fucoxanthin; N-acylated proteins; N-acylated peptides, such as Matrixyl™; N-acylated amino acids; partial hydrolyzates of N-acylated proteins; amino acids; peptides; total hydrolyzates of proteins; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or marine algae; marine plant extracts; marine extracts in general, such as corals; essential waxes; bacterial extracts; ceramides; phospholipids; compounds showing an antimicrobial action or a purifying action, such as Lipacide™ CBG, Lipacide™ UG, Sepicontrol™ A5; Octopirox™ or Sensiva™ SC50; compounds showing an energizing or stimulating property, such as Physiogenyl™, panthenol and its derivatives, such as Sepicap™ MP; antiaging active principles, such as Sepilift™ DPHP, Lipacide™ PVB, Sepivinol™, Sepivital™, Manoliva™, Phyto-Age™, Timecode™; Survicode™; antiphotoaging active principles; active principles which protect the integrity of the dermoepidermal junction; active principles which increase the synthesis of the components of the extracellular matrix, such as collagen, elastins or glycosaminoglycans; active principles which act favorably on chemical cell communication, such as cytokines, or physical cell communication, such as integrins; active principles which create a feeling of "heating" on the skin, such as activators of cutaneous microcirculation (such as nicotinic acid derivatives) or products which create a feeling of "coolness" on the skin (such as menthol and derivatives); active principles which improve cutaneous microcirculation, for example venotonics; draining active principles; active principles having a decongestant purpose, such as *Ginkgo biloba*, ivy, horse chestnut, bamboo, Ruscus, butcher's broom, *Centella asiatica*, fucus, rosemary or willow extracts; agents for tanning or browning the skin, for example dihydroxyacetone (DHA), erythrulose, mesotartaric aldehyde, glutaraldehyde, glyceraldehyde, alloxan or ninhydrin, plant extracts, for example extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in the European patent application EP 0 971 683; agents known for their action in facilitating and/or accelerating tanning and/or browning of human skin, and/or for their action in coloring human skin, for example carotenoids (and more particularly β-carotene and γ-carotene), the product sold under the brand name Carrot Oil (INCI name: *Daucus carota, Helianthus annuus* sunflower oil) by Provital, which contains carotenoids, vitamin E and vitamin K; tyrosine and/or its derivatives, known for their effect on the acceleration of the tanning of human skin in combination with exposure to ultraviolet radiation, for example the product sold under the brand name "SunTan Accelerator™" by Provital, which contains tyrosine and riboflavins (vitamin B), the tyrosine and tyrosinase complex sold under the brand name "Zymo Tan Complex" by Zymo Line, the product sold under the band name MelanoBronze™ (INCI name: Acetyl Tyrosine, Monk's pepper extract (*Vitex agnus-castus*)) by Mibelle, which contains acetyl tyrosine, the product sold under the brand name Unipertan VEG-24/242/2002 (INCI name: butylene glycol and acetyl tyrosine and hydrolyzed vegetable protein and adenosine triphosphate) by Unipex, the product sold under the brand name "Try-Excell™" (INCI name: Oleoyl Tyrosine and Luffa Cylindrica (Seed Oil and Oleic Acid) by Sederma, which contains extracts of marrow seed (or loofah oil), the product sold under the brand name "Actibronze™" (INCI name: hydrolyzed wheat protein and acetyl tyrosine and copper gluconate) by Alban Muller, the product sold under the brand name Tyrostan™ (INCI name: potassium caproyl tyrosine) by Synerga, the product sold under the brand name Tyrosinol (INCI name: sorbitan isostearate, glyceryl oleate, caproyl tyrosine) by Synerga, the product sold under the brand name InstaBronze™ (INCI name: dihydroxyacetone and acetyl tyrosine and copper gluconate) by Alban Muller, the product sold under the brand name Tyrosilane (INCI name: methylsilanol and acetyl tyrosine) by Exymol; peptides known for their melanogenesis-activating effect, for example the product sold under the brand name Bronzing SF Peptide powder (INCI name: Dextran and Octapeptide-5) by Infinitec Activos, the product sold under the brand name Melitane (INCI name: Glycerin and Aqua and Dextran and Acetyl Hexapeptide-1) comprising acetyl hexapeptide-1 known for its α-MSH agonist action, the product sold under the brand name Melatimes Solutions™ (INCI name: Butylene Glycol, Palmitoyl Tripeptide-40) by Lipotec, sugars and sugar derivatives, for example the product sold under the brand name Tanositol™ (INCI name: inositol) by Provital, the product sold under the brand name Thalitan™ (or Phycosaccharide™ AG) by CODIF International (INCI name: aqua and hydrolyzed algin (*Laminaria digitata*) and magnesium sulfate and manganese sulfate) containing an oligosaccharide of marine origin (guluronic acid and mannuronic acid which are chelated with magnesium and manganese ions), the product sold under the brand name Melactiva™ (INCI name: Maltodextrin, Mucuna Pruriens Seed Extract) by Alban Muller, flavonoid-rich compounds, for example the product sold under the brand name "Biotanning" (INCI name: Hydrolyzed citrus Aurantium dulcis fruit extract) by Silab and known to be rich in lemon flavonoids (of the hesperidin type); agents intended for the treatment of head hair and/or body hair, for example agents which protect the melanocytes of the hair follicle, which are intended to protect said melanocytes against cytotoxic agents responsible for the senescence and/or the apoptosis of said melanocytes, such as mimetics of the activity of DOPAchrome tautomerase chosen from those described in the European patent application published under the number EP 1 515 688 A2, synthetic molecules which mimic SOD, for example manganese complexes, antioxidant compounds, for example cyclodextrin derivatives, silica-containing compounds derived from ascorbic acid, lysine pyrrolidonecarboxylate or arginine pyrrolidonecarboxylate, combinations of mono- and diester of cinnamic acid and of vitamin C, and more generally those mentioned in the European patent application published under the number EP 1 515 688 A2.

Examples of antioxidants which can be combined with said self-invertible inverse latex as defined above in said compositions (F) and (G) include EDTA and its salts, citric acid, tartaric acid, oxalic acid, BHA (butylhydroxyanisole), BHT (butylhydroxytoluene), tocopherol derivatives, such as tocopheryl acetate, mixtures of antioxidant compounds, such as Dissolvine GL 47S sold by AkzoNobel under the INCI name: Tetrasodium Glutamate Diacetate.

Examples of sunscreens which can be combined with said self-invertible inverse latex as defined above in said compositions (F) and (G) include all those appearing in the amended Cosmetics Directive 76/768/EEC, Annex VII.

The organic sunscreens which can be combined with said self-invertible inverse latex as defined above in said compositions (F) and (G) include the family of the benzoic acid derivatives, such as para-aminobenzoic acids (PABA), in particular monoglycerol esters of PABA, ethyl esters of N,N25 propoxy PABA, ethyl esters of N,N-diethoxy PABA, ethyl esters of N,N-dimethyl PABA, methyl esters of N,N-dimethyl PABA or butyl esters of N,N-dimethyl PABA; the family of the anthranilic acid derivatives, such as homomenthyl N-acetylanthranilate; the family of the salicylic acid derivatives, such as amyl salicylate, homomenthyl salicylate, ethylhexyl salicylate, phenyl salicylate, benzyl salicylate or p-isopropylphenyl salicylate; the family of the cinnamic acid derivatives, such as ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate or mono(2-ethylhexanoyl)glyceryl di(para-methoxycinnamate); the family of the benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2,5-dicarboxylate, 2-hydroxy-4-(n-octyloxy)benzophenone, 4-hydroxy-3-carboxybenzophenone; 3-(4'-methylbenzylidene)-d,l-camphor, 3-benzylidene-d,l-camphor, camphor benzalkonium methosulfate; urocanic acid, ethyl urocanate; the family of the sulfonic acid derivatives, such as 2-phenylbenzimidazole-5-sulfonic acid and its salts; the family of the triazine derivatives, such as hydroxyphenyl triazine, ethylhexyloxyhydroxyphenyl-4-methoxyphenyltriazine, 2,4,6-trianilino(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis-(2-ethylhexyl) ester of benzoic acid, 2-phenyl-5-methylbenzoxazole, 2,2'-hydroxy-5-methylphenylbenzotriazole, 2-(2'-hydroxy-5'-(t-octyl)phenyl)benzotriazole, 2-(2'-hydroxy-5'-methyphenyl)benzotriazole; dibenzalazine; dianisoylmethane, 4-methoxy-4"-t-butylbenzoylmethane; 5-(3,3-dimethyl-2-norbornylidene)-3-pentan-2-one; the family of the diphenylacrylate derivatives, such as 2-ethylhexyl 2-cyano-3,3-diphenyl-2-propenoate or ethyl 2-cyano-3,3-diphenyl-2-propenoate; or the family of the polysiloxanes, such as benzylidene siloxane malonate.

The inorganic sunscreens, also known as "inorganic filters", which can be combined with said self-invertible inverse latex as defined above in said compositions (F) and (G) include titanium oxides, zinc oxides, cerium oxide, zirconium oxide, yellow, red or black iron oxides, or chromium oxides. These inorganic filters may or may not be micronized, may or may not have been subjected to surface treatments and may optionally be presented in the form of aqueous or oily predispersions.

Finally, a subject matter of the invention is the use of said composition ($C_e$), as defined above, as inverting agent of an inverse latex of a crosslinked anionic polyelectrolyte (P) comprising, per 100 mol %:

($a_1$)—of a proportion of greater than or equal to 30 mol % and less than or equal to 100 mol % of monomer units resulting from 2-methyl-2-[(1-oxo-2-propenyl)amino]-1-propanesulfonic acid in free acid or partially or totally salified form;

($a_2$)—optionally of a proportion of greater than 0 mol % and less than or equal to 70 mol % of monomer units resulting from at least one monomer chosen from the elements of the group consisting of acrylic acid, methacrylic acid, 2-(carboxyethyl)acrylic acid, itaconic acid, maleic acid and 3-methyl-3-[(1-oxo-2-propenyl)amino]butanoic acid, the carboxyl functional group of said monomers being in the free acid, partially salified or completely salified form, and/or from the elements of the group consisting of 2-hydroxyethyl acrylate, 2,3-dihydroxypropyl acrylate, 2-hydroxyethyl methacrylate, 2,3-dihydroxypropyl methacrylate, or vinylpyrrolidone;

($a_3$)—of a proportion of greater than 0 mol % and less than or equal to 1 mol % of monomer units resulting from at least one diethylenic or polyethylenic crosslinking monomer (AR);

the sum of said molar proportions of monomer units according to $a_1$), $a_2$) and $a_3$) being equal to 100 mol %;

said inverse latex being an emulsion of water-in-oil type (W) comprising, per 100% of its weight:

a)—from 10% by weight to 90% by weight of said crosslinked anionic polyelectrolyte (P);

b)—from 5% by weight to 50% by weight of a fatty phase constituted of at least one oil (O);

c)—from 1% by weight to 50% by weight of water; and d)—from 0.5% by weight to 10% by weight of an emulsifying system of water-in-oil type ($S_1$);

the sum of the proportions by weight of compounds according to a), b), c) and d) being equal to 100% by weight.

DESCRIPTION OF THE PREFERRED EMBODIMENTS

The following examples illustrate the invention without, however, limiting it.

I—Preparation of Surface-Active Compositions According to the Invention and Comparative Compositions

$I_A$—Preparation of a Composition Comprising Glyceryl Polyglucoside and Glycerol 650 grams of glycerol, i.e. 5 molar equivalents, are introduced into a jacketed glass reactor provided with efficient stirring, in which jacket a heat-exchange fluid circulates. The glycerol is brought to a temperature of approximately 100° C.

423.9 grams, i.e. 1 molar equivalent, of glucose are then gradually added to the reaction medium in order to allow it to homogeneously disperse. An acidic catalytic system consisting of 0.51 gram of 98% sulfuric acid is added to the mixture thus obtained.

The reaction medium is placed under a partial vacuum at 30 mbars, and maintained at a temperature of 100° C.-105° C. for a period of time of four hours, with evacuation of the water formed by means of a distillation assembly.

The reaction medium is subsequently cooled to 95° C.-100° C. and neutralized by addition of 30% sodium hydroxide, in order to bring the pH of a 1% solution of this mixture to a value of approximately 7.0.

The reaction mixture is emptied in order to obtain the composition referenced ($E_{IB}$).

The analytical characteristics of the composition ($E_{IB}$) thus obtained are as follows:

Appearance (visual): clear liquid;
pH 1% solution: 6.8;
Residual glycerol: 55.1%;
Residual glucose: <1%;
Glyceryl polyglucosides: 44.7%

$I_B$—Preparation of the Composition ($EM_2$) Based on Decaglycerol Laurate ($EM_1$) and on Hexaglycerol 71.5 grams of decaglycerol monolaurate sold under the brand name Decaglyn 1-L (hereinafter denoted by the term "Composition ($EM_1$)") and 28.5 grams of polyglycerol-6 (sold under the brand name Polyglycerol 6™ by Spiga) are introduced into a jacketed glass reactor provided with efficient mechanical stirring, in which jacket a heat-exchange fluid circulates, at a temperature of 35° C. under mechanical stirring of anchor type at a speed of 80 revolutions/minute. After mixing under such conditions for 30 minutes, the mixture is emptied in order to obtain the composition ($EM_2$).

$I_C$—Preparation of the Composition ($EM_3$) Based on Decaglycerol Laurate ($EM_1$) and on Decaglycerol 71.5 grams of decaglycerol monolaurate sold under the brand name Decaglyn 1-L (hereinafter denoted by the term "Composition ($EM_1$)") and 28.5 grams of polyglycerol-10 (sold under the brand name Polyglycerin 10™) are introduced into a jacketed glass reactor provided with efficient mechanical stirring, in which jacket a heat-exchange fluid circulates, at a temperature of 35° C. under mechanical stirring of anchor type at a speed of 80 revolutions/minute. After mixing under such conditions for 30 minutes, the mixture is emptied in order to obtain the composition ($EM_3$).

$I_D$—Preparation of the Composition ($EM_4$) Based on Decaglycerol Laurate ($EM_1$), on Glyceryl Polyglucoside and on Glycerol ($E_{IB}$)

71.5 grams of decaglycerol monolaurate sold under the brand name Decaglyn 1-L (hereinafter denoted by the term "Composition ($EM_1$)") and 28.5 grams of the composition ($E_{IB}$), the preparation of which is described above, are introduced into a jacketed glass reactor provided with efficient mechanical stirring, in which jacket a heat-exchange fluid circulates, at a temperature of 35° C. under mechanical stirring of anchor type at a speed of 80 revolutions/minute. After mixing under such conditions for 30 minutes, the mixture is emptied in order to obtain the composition ($EM_4$).

$I_E$—Preparation of the Composition ($EM_5$) Based on Decaglycerol Laurate ($EM_1$) and on Glycerol 71.5 grams of decaglycerol monolaurate sold under the brand name Decaglyn 1-L (hereinafter denoted by the term "Composition ($EM_1$)") and 28.5 grams of glycerol are introduced into a jacketed glass reactor provided with efficient mechanical stirring, in which jacket a heat-exchange fluid circulates, at a temperature of 35° C. under mechanical stirring of anchor type at a speed of 80 revolutions/minute. After mixing under such conditions for 30 minutes, the mixture is emptied in order to obtain the composition ($EM_5$).

The analytical characteristics of the compositions ($EM_1$), ($EM_2$), ($EM_3$), ($EM_4$), ($EM_5$) and ($EM_6$) are recorded in table 1 below.

TABLE 1

| Proportions of constituents (% by weight) | Emulsifying composition | | | | |
|---|---|---|---|---|---|
| | ($EM_1$) | ($EM_2$) | ($EM_3$) | ($EM_4$) | ($EM_5$) |
| Decaglycerol monolaurate | 100% | 71.5% | 71.5% | 71.5% | 71.5% |
| Proportion by weight of hexaglycerol | 0% | 28.5 | 0% | 0% | 0% |
| Proportion by weight of decaglycerol | 0% | 0% | 28.5 | 0% | 0% |
| Proportion by weight of glyceryl polyglucoside | 0% | 0% | 0% | 12.8% | 0% |
| Proportion by weight of glycerol | 0% | 0% | 0% | 15.7% | 28.5 |

II—Preparation and Evaluation of Self-Invertible Inverse Latexes of a Crosslinked Copolymer of the Sodium Salt of 2-methyl-[(1-oxo-2-propenyl)amino]-1-propanesulfonic Acid and of Partially Salified Acrylic Acid An aqueous phase is prepared by successively pouring, into a beaker and with stirring, 75.4 grams of glacial acrylic acid, 577.5 grams of a 55% aqueous solution of sodium salt of 2-methyl-[(1-oxo-2-propenyl)amino]-1-propanesulfonic acid, 42.5 grams of a 48% by weight aqueous sodium hydroxide solution, 0.45 gram of a commercial 40% by weight aqueous sodium diethylenetriaminepentaacetate solution and 0.167 gram of methylenebis(acrylamide). The pH of this aqueous phase is subsequently adjusted to 5.5.

Independently, an organic phase is prepared by mixing 208 grams of the mixture of alkanes sold under the brand name Emogreen™ L15, 14 grams of Montane™ 80, 9.5 grams of Montane™ 70 and 0.2 gram of azobis(isobutyronitrile) (AIBN).

The aqueous phase prepared is subsequently gradually added to the oily phase and then dispersed using a rotor-stator of Ultra-Turrax type sold by IKA.

The emulsion obtained is transferred into a reactor in order to be subjected to sparging with nitrogen in order to remove the oxygen and cooled to approximately 5-6° C. 5 cm$^3$ of a 0.42% by weight solution of cumene hydroperoxide in Emogreen™ L15 are added to the emulsion which is kept stirred, followed by gradual introduction of a 0.1% by weight aqueous sodium metabisulfite solution at a flow rate of 0.5 cm$^3$ per minute, in order to initiate the polymerization reaction. The temperature of the medium increases until a stationary phase is reached. The reaction medium is subsequently heated at 85° C. for 1 hour and then the combined mixture is cooled down to approximately 35° C. in order to obtain the mixture denoted ($M_2$).

The mixture ($M_2$) obtained above is divided up into different portions, to which the different surface-active compositions ($EM_1$), ($EM_2$), ($EM_3$), ($EM_4$) and ($EM_5$), as described above, preheated to 60° C., are added in proportions by weight as shown in table 2 below.

The self-invertible inverse latexes resulting from these mixtures are respectively denoted ($IL_1$), ($IL_2$), ($IL_3$), ($IL_4$) and ($IL_5$) and are evaluated by the observation of their appearance at 25° C., by the rate of inversion during the preparation of an aqueous gel comprising 2% by weight of self-invertible inverse latex and by the viscosity of this aqueous gel comprising 2% by weight of a self-invertible inverse latex.

The method for evaluation of the duration of inversion of the self-invertible inverse latexes consists in introducing, into a 2 liter beaker, the amount of water necessary for the preparation of 800 grams of an aqueous gel. A mechanical helical stirrer of Turbotest™ type, version 2004, sold by VMI, connected to a motor, is placed toward the bottom of the beaker. Stirring is started at a speed of 900 revolutions/minute and the necessary amount of self-invertible inverse latex to be evaluated is introduced into the beaker with stirring. This stirring creates a vortex which disappears when the polymer inverts and the gel is formed. The duration of inversion, measured in seconds, of the self-invertible inverse latexes corresponds to the time elapsed between the start of the addition of the self-invertible inverse latex tested and the disappearance of the vortex, resulting in a smooth gel, devoid of lumps, being obtained. This evaluation is carried out on conclusion of the manufacture of the inverse latexes tested (t=0) and then after a period of storage at 25° C. of 3 months (t=3 months). The results obtained are recorded in table 2 below. The viscosity of an aqueous gel comprising 2% by weight of self-invertible inverse latex ($\mu$) is measured at t=0 and then at t=3 months, by means of a Brookfield RVT viscometer (Spindle 6 Speed 5). Likewise, the appearance of the self-invertible inverse latex is evaluated visually at t=0.

TABLE 2

| | Self-invertible inverse latexes | | | | |
|---|---|---|---|---|---|
| | ($IL_1$) | ($IL_2$) | ($IL_3$) | ($IL_4$) | ($IL_5$) |
| | Reference of the surface-active composition tested | | | | |
| | ($EM_1$) | ($EM_2$) | ($EM_3$) | ($EM_4$) | ($EM_5$) |
| Amount tested ($EM_i$)/($IL_i$) (% by weight) | 5% | 7% | 7% | 7% | 7% |
| Measurements at t = 0 | | | | | |
| $\mu$ (in mPa · s) | 120 000 | 116 000 | 104 000 | 98 000 | 104 000 |
| Duration of inversion | 130 s | 38 s | 38 s | 60 s | 16 s |
| Appearance of the self-invertible latex at 25° C. | Lme* | Lme* | Lme* | Lme* | Lme* |
| Measurements at t = 3 months (3 M) | | | | | |
| $\mu$ (in mPa · s) | 97 000 | 98 000 | 100 000 | 94 000 | 95 000 |
| Duration of inversion | 151 s | 55 s | 78 s | 78 s | 17 s |

Lme*: Liquid milky emulsion

The self-invertible inverse latexes ($IL_2$), ($IL_3$), ($IL_4$) and ($IL_5$) according to the invention and devoid of alkoxylated derivatives and more particularly of ethoxylated derivatives make it possible to obtain smooth gels, with a duration of inversion far lower than that observed for the self-invertible inverse latex ($IL_1$), comprising only decaglycerol monolaurate alone as constituent of the inverting surface-active system, while retaining excellent thickening properties. Furthermore, they are characterized by a better reproducibility of the rate of inversion and of the thickening properties after storage for three months than for the comparative self-invertible inverse latex ($IL_1$).

III—Preparation and Evaluation of Self-Invertible Inverse Latexes of a Crosslinked Copolymer of the Sodium Salt of 2-methyl-[(1-oxo-2-propenyl)amino]-1-propanesulfonic Acid and of Partially Salified Acrylic Acid Example II, described above, is repeated, the 208 grams of Emogreen™ L15 being replaced with 208 grams of isohexadecane, in order to obtain the mixture denoted ($M_3$), which is divided up into different portions, to which the different surface-active compositions ($EM_1$), ($EM_2$) and ($EM_3$), as described above, preheated to 60° C., are added in proportions by weight as shown in table 3 below. The self-invertible inverse latexes resulting from these mixtures are respectively denoted ($IL_6$), ($IL_7$) and ($IL_8$) and are evaluated by the observation of their appearance at 25° C., by the rate of inversion during the preparation of an aqueous gel comprising 2% by weight of self-invertible inverse latex (the method of which is described above) and by the viscosity of this aqueous gel comprising 2% by weight of a self-invertible inverse latex (μ; Brookfield RVT viscometer (Spindle 6 Speed 5)). This evaluation is carried out on conclusion of the manufacture of the inverse latexes tested (t=0) and then after a period of storage at 25° C. of 3 months (t=3 months).

The results obtained are recorded in table 3 below.

TABLE 3

| | Self-invertible inverse latexes | | |
|---|---|---|---|
| | ($IL_6$) | ($IL_7$) | ($IL_8$) |
| | Surface-active composition tested | | |
| | ($EM_1$) | ($EM_2$) | ($EM_3$) |
| Amount tested ($EM_i$)/($IL_i$) (% by weight) | 5% | 7% | 7% |
| Measurements at t = 0 | | | |
| μ (in mPa · s) | 108 000 | 106 000 | 110 000 |
| Duration of inversion | 125 s | 60 s | 25 s |
| Appearance of the self-invertible latex at 25° C. | Lme* | Lme* | Lme* |
| Measurements at t = 3 months | | | |
| μ (in mPa · s) | 97 000 | 102 000 | 105 000 |
| Duration of inversion | 155 s | 70 s | 72 s |

Lme*: Liquid milky emulsion

The self-invertible inverse latexes ($IL_7$) and ($IL_8$) according to the invention and devoid of alkoxylated derivatives and more particularly of ethoxylated derivatives make it possible to obtain smooth gels, with a duration of inversion far lower than that observed for the self-invertible inverse latex ($IL_6$), comprising only decaglycerol monolaurate alone as constituent of the inverting surface-active system, while retaining excellent thickening properties. Furthermore, they are characterized by a better reproducibility of the rate of inversion and of the thickening properties after storage for three months than for the comparative self-invertible inverse latex ($IL_1$).

IV: Illustrative Cosmetic Formulations

In the following formulations, the percentages are expressed as percentage by weight per 100% of the weight of the formulation.

Example IV-1

Care Cream

Cyclomethicone: 10%
Self-invertible inverse latex ($IL_2$): 0.8%
Montanov™ 68: 2%
Stearyl alcohol: 1%
Stearic alcohol: 0.5%
Preservative: 0.65%
Lysine: 0.025%
EDTA (disodium salt): 0.05%
Xanthan gum: 0.2%
Glycerol: 3%
Water: q.s. for 100%

Example IV-2

Antisun Milk

Formula
A Montanov™ 68: 3.0%
Sesame oil: 5.0%
Parsol™ MCX: 5.0%
λ-Carrageenan: 0.10%
B Water: q.s. for
C Self-invertible inverse latex ($IL_3$): 0.80%
D Fragrance: q.s.
Preservative: q.s.
Procedure
  Emulsify B in A at 60° C., then add C at approximately 60° C., then D at approximately 30° C. and adjust the pH, if necessary.

Example IV-3

Body Milk

Montanov™ 202: 3.5%
Lanol™ 37T: 8.0%
Solagum™ L: 0.05%
Water: q.s. for
Benzophenone-3: 2.0%
Dimethicone 350 cPs: 0.05%
Self-invertible inverse latex ($IL_2$): 2.5%
Preservative: 0.2%
Fragrance: 0.4%

Example IV-4

Makeup-Removing Emulsion Comprising Sweet Almond Oil

Montanov™ 202: 5%
Sweet almond oil: 5%
Water: q.s. for 100%
Self-invertible inverse latex ($IL_2$): 0.3%
Glycerol: 5%
Preservative: 0.2%
Fragrance: 0.3%

Example IV-5

Moisturizing Cream for Greasy Skin

Montanov™ 68: 5%
Cetylstearyl octanoate: 8%
Octyl palmitate: 2%
Water: q.s. for 100%
Self-invertible inverse latex ($IL_4$): 2.6%
Micropearl™ M100: 3.0%
Mucopolysaccharides: 5%
Sepicide™ HB: 0.8%
Fragrance: 0.3%

Example IV-6

Makeup-Removing Milk

Montanov™ 68: 3%
Primol™ 352: 8.0%
Sweet almond oil: 2%
Water: q.s. for 100%
Self-invertible inverse latex ($IL_2$): 0.8%
Preservative: 0.2%

Example IV-7

Antisun Milk

Montanov™ L: 3.5%
Lanol™ 37T: 10.0%
Parsol™ MCX: 5.0%
Eusolex™ 4360: 2.0%
Water: q.s. for 100%
Self-invertible inverse latex ($IL_2$): 1.8%
Preservative: 0.2%
Fragrance: 0.4%

Example IV-8

Sunless Tanning Emulsion

Lanol™ 99: 15%
Montanov™ 68: 3.0%
Parsol™ MCX: 3.0%
Water: q.s. for 100%
Dihydroxyacetone: 5.0%
Monosodium phosphate: 0.2%
Self-invertible inverse latex ($IL_5$): 2.5%
Fragrance: 0.3%
Sepicide™ HB: 0.8%
Sodium hydroxide: q.s. pH=5

Example IV-9

Care Cream

Cyclomethicone: 10%
Self-invertible inverse latex ($IL_4$): 2.8%
Montanov™ 202: 4.5%
Preservative: 0.65%
Lysine: 0.025%
EDTA (disodium salt): 0.05%
Xanthan gum: 0.2%
Glycerol: 3%
Water: q.s. for 100%

Example IV-10

Antisun Cream

Simulsol™ 165: 3%
Montanov™ 68: 2%
C12-C15 benzoate: 8%
Pecosil™ PS 100: 2%
Dimethicone: 2%
Cyclomethicone: 5%
Octyl para-methoxycinnamate: 6%
Benzophenone-3: 4%
Titanium oxide: 8%
Xanthan gum: 0.2%
Butylene glycol: 5%
Demineralized water: q.s. for 100%
Self-invertible inverse latex ($IL_2$): 1.5%
Preservative, fragrance: q.s.

Example IV-11

Antisun and Self-Tanning Gel

Montanov™ 68: 3.0%
Glyceryl triheptanoate: 10.0%
Deepaline™ PVB: 1.05%
Self-invertible inverse latex ($IL_2$): 2.2%
Water: q.s. 100%
Dihydroxyacetone: 5%
Fragrance: 0.1%
Sepicide™ HB: 0.3%
Sepicide™ CI: 0.1%
Parsol™ MCX: 4.0%

The definitions of the products used in the examples are as follows:

Micropearl™ M 100 is an ultrafine powder which is very soft to the touch and which has a mattifying action, sold by Matsumo.

Sepicide™ CI, imidazolidinyl urea, is a preservative sold by Seppic.

Simulsol™ 165 is self-emulsifying glycerol stearate, sold by Seppic.

Sepicide™ HB, a mixture of phenoxyethanol, methylparaben, ethylparaben, propylparaben and butylparaben, is a preservative sold by Seppic.

Parsol™ MCX is octyl para-methoxycinnamate, sold by Givaudan.

Lanol™ 37T is glycerol triheptanoate, sold by Seppic.

Solagum™ L is a carrageenan, sold by Seppic.

Eusolex™ 4360 is a sunscreen, sold by Merck.

Deepaline™ PVB is an acylated wheat protein hydrolyzate, sold by Seppic.

Primol™ 352 is a mineral oil, sold by Exxon.

Pecosil™ PS 100 is Dimethicone PEG-7, sold by Phoenix.

Montanov™ 68 (INCI name: cetearyl alcohol (and) cetearyl glucoside) is an emulsifying agent, sold by Seppic.

Montanov™ L (INCI name: C14-22 alcohols (and) C12-20 alkyl glucoside) is an emulsifying agent, sold by Seppic.

Montanov™ 202 (INCI name: arachidyl alcohol & behenyl alcohol & arachidyl) is an emulsifying agent, sold by Seppic.

The invention claimed is:

1. A self-invertible inverse latex of a crosslinked anionic polyelectrolyte (P) comprising, per 100 mol %:
   ($a_1$)—of a proportion of greater than or equal to 30 mol % and less than 100 mol % of monomer units resulting from 2-methyl-2-[(1-oxo-2-propenyl)amino]-1-propanesulfonic acid in free acid or partially or totally salified form;
   ($a_2$)—of a proportion of greater than 0 mol % and less than or equal to 70 mol % of monomer units resulting from at least one monomer chosen from the elements of the group consisting of acrylic acid, methacrylic acid, 2-(carboxyethyl)acrylic acid, itaconic acid, maleic acid and 3-methyl-3-[(1-oxo-2-propenyl)amino]butanoic acid, the carboxyl functional group of said monomers being in the free acid, partially salified or completely salified form, and/or from the elements of the group consisting of 2-hydroxyethyl acrylate, 2,3-dihydroxypropyl acrylate, 2-hydroxyethyl methacrylate, 2,3-dihydroxypropyl methacrylate, or vinylpyrrolidone;

(a$_3$)—of a proportion of greater than 0 mol % and less than or equal to 1 mol % of monomer units resulting from at least one diethylenic or polyethylenic crosslinking monomer (AR);

the sum of said molar proportions of monomer units according to a$_1$), a$_2$) and a$_3$) being equal to 100 mol %;

said self-invertible inverse latex being an emulsion of water-in-oil (W) comprising, per 100% of its weight:

a)—from 10% by weight to 90% by weight of said crosslinked anionic polyelectrolyte (P);

b)—from 5% by weight to 50% by weight of a fatty phase constituted of at least one oil (O);

c)—from 1% by weight to 50% by weight of water;

d)—from 0.5% by weight to 10% by weight of an emulsifying system of water-in-oil (S$_1$); and e)—from 2% by weight to 10% by weight of an emulsifying system of oil-in-water (S$_2$);

the sum of the proportions by weight of a), b), c), d) and e) being equal to 100% by weight;

wherein said emulsifying system of oil-in-water (S$_2$) comprises, per 100% of its weight:

f)—a proportion of greater than or equal to 50% by weight and less than or equal to 100% of a composition (C$_e$) which comprises, per 100% of its weight;

e$_1$)—from 5% by weight to 15% by weight of at least one compound of formula (I):

$$HO—[CH_2—CH(OH)—CH_2—O]_n—H \quad (I)$$

in which n represents an integer greater than or equal to 1 and less than or equal to 15;

e$_2$)—from 60% by weight to 80% by weight of at least one compound of formula (II):

$$R_1—(C=O)—[O—CH_2—CH(OH)—CH_2]_p—OH \quad (II),$$

in which p, which is different from or identical to n, represents an integer greater than or equal to 1 and less than or equal to 15; and in which the R$_1$—(C=O)— group represents a saturated or unsaturated and linear or branched aliphatic radical comprising from 6 to 22 carbon atoms; and e$_3$)—from 5% to 15% by weight of at least one composition (C$_{11}$) represented by the formula (III):

$$HO—[CH_2—CHOH—CH_2—O-]_q-(G)_r-H \quad (III),$$

in which q, which is different from or identical to n, represents an integer greater than or equal to 1 and less than or equal to 3, G represents the residue of a reducing sugar and r represents a decimal number greater than or equal to 1.05 and less than or equal to 5.00;

said composition (C$_{11}$) consisting of a mixture of the compounds of formulae (III$_1$), (III$_2$), (III$_3$), (III$_4$) and (III$_5$):

$$HO—[CH_2—CHOH—CH_2—O—]_q—O-(G)_1-H \quad (III_1),$$

$$HO—[CH_2—CHOH—CH_2—O—]_q—O-(G)_2-H \quad (III_2),$$

$$HO—[CH_2—CHOH—CH_2—O—]_q—O-(G)_3-H \quad (III_3),$$

$$HO—[CH_2—CHOH—CH_2—O—]_q—O-(G)_4-H \quad (III_4),$$

$$HO—[CH_2—CHOH—CH_2—O—]_q—O-(G)_5-H \quad (III_5),$$

in molar proportions of said compounds of formulae (III$_1$), (III$_2$), (III$_3$), (III$_4$) and (III$_5$) respectively equal to a$_1$, a$_2$, a$_3$, a$_4$ and a$_5$, such that the sum (a$_1$+a$_2$+a$_3$+a$_4$+a$_5$) is equal to 1, and that the sum (a$_1$+2a$_2$+3a$_3$+4a$_4$+5a$_5$) is equal to r;

the sum of the proportions by weight of e$_1$), e$_2$) and e$_3$) being equal to 100% by weight.

2. The self-invertible inverse latex as defined in claim 1, wherein said crosslinked anionic polyelectrolyte (P) is a a copolymer of 2-methyl-2-[(1-oxo-2-propenyl)amino]-1-propanesulfonic acid and of acrylic acid which are partially or completely salified in the sodium salt or ammonium salt form, crosslinked by triallylamine and/or methylenebis(acrylamide); a copolymer of 2-methyl-2-[(1-oxo-2-propenyl)amino]-1-propanesulfonic acid (γ) partially or completely salified in the sodium salt form and of acrylic acid (δ) partially or completely salified in the sodium salt form in a molar ratio (γ)/(δ) of greater than or equal to 30/70 and less than or equal to 90/10, crosslinked by triallylamine and/or methylenebis(acrylamide); or a copolymer of 2-methyl-2-[(1-oxo-2-propenyl)amino]-1-propanesulfonic acid (γ) partially or completely salified in the sodium salt form and of acrylic acid (δ) partially or completely salified in the sodium salt form in a molar ratio (γ)/(δ) of greater than or equal to 40/60 and less than or equal to 90/10, crosslinked by triallylamine and/or methylenebis(acrylamide).

3. The self-invertible inverse latex as defined in either claim 1, wherein, in the formula (I) as defined above, n represents an integer greater than or equal to 1 and less than or equal to 10, and wherein, in the formula (II) as defined above, p, which is identical to or different from n, represents an integer greater than or equal to 1 and less than or equal to 10, and the R$_1$—(C=O)— group is chosen from octanoyl, decanoyl, W-undecylenoyl, dodecanoyl, tetradecanoyl, hexadecanoyl, octadecanoyl, 9-octadecenoyl or 9,12-octadecadienoyl radicals.

4. The self-invertible inverse latex as defined in claim 1, wherein, in said emulsifying system of oil-in-water (S$_2$), said composition (C$_e$) as defined above consists of, per 100% of its weight:

e$_1$)—from 5% by weight to 15% by weight of at least one compound of formula (I):

as defined above;

e$_2$)—from 60% by weight to 80% by weight of at least one compound of formula (II) as defined above; and e$_3$)—from 5% to 15% by weight of at least one composition (C$_{11}$) represented by the formula (III):

$$HO—[CH_2—CHOH—CH_2—O-]_q-(G)_r-H \quad (III),$$

in which q, which is different from or identical to n, represents an integer greater than or equal to 1 and less than or equal to 3, G represents the residue of a reducing sugar and r represents a decimal number greater than or equal to 1.05 and less than or equal to 5.00;

said composition (C$_{11}$) consisting of a mixture of the compounds of formulae (III$_1$), (III$_2$), (III$_3$), (III$_4$) and (III$_5$):

$$HO—[CH_2—CHOH—CH_2—O—]_q—O-(G)_1-H \quad (III_1),$$

$$HO—[CH_2—CHOH—CH_2—O—]_q—O-(G)_2-H \quad (III_2),$$

$$HO—[CH_2—CHOH—CH_2—O—]_q—O-(G)_3-H \quad (III_3),$$

$$HO—[CH_2—CHOH—CH_2—O—]_q—O-(G)_4-H \quad (III_4),$$

$$HO—[CH_2—CHOH—CH_2—O—]_q—O-(G)_5-H \quad (III_5),$$

in molar proportions of said compounds of formulae (III$_1$), (III$_2$), (III$_3$), (III$_4$) and (III$_5$) respectively equal to a$_1$, a$_2$, a$_3$, a$_4$ and a$_5$, such that the sum (a$_1$+a$_2$+a$_3$+a$_4$+a$_5$) is equal to 1, and that the sum (a$_1$+2a$_2$+3a$_3$+4a$_4$+5a$_5$) is equal to r;

the sum of the proportions by weight of e$_1$), e$_2$) and e$_3$) being equal to 100% by weight.

5. The self-invertible inverse latex as defined in claim 1, wherein, in the formula (III) as defined above, q is equal to 1, G represents the residue of glucose and r represents a decimal number greater than or equal to 1.05 and less than or equal to 2.5.

6. The self-invertible inverse latex as defined in claim 2, wherein, in the formula (I) as defined above, n represents an integer greater than or equal to 1 and less than or equal to 10, and wherein, in the formula (II) as defined above, p, which is identical to or different from n, represents an integer greater than or equal to 1 and less than or equal to 10, and the R1-(C=O)—group is chosen from octanoyl, decanoyl, ω-undecylenoyl, dodecanoyl, tetradecanoyl, hexadecanoyl, octadecanoyl, 9-octadecenoyl or 9,12-octadecadienoyl radicals.

7. A self-invertible inverse latex of a crosslinked anionic polyelectrolyte (P) comprising, per 100 mol %:
- ($a_1$)—of a proportion of greater than or equal to 30 mol % and less than 100 mol % of monomer units resulting from 2-methyl-2-[(1-oxo-2-propenyl)amino]-1-propanesulfonic acid in free acid or partially or totally salified form; and
- ($a_2$)—of a proportion of greater than 0 mol % and less than or equal to 1 mol % of monomer units resulting from at least one diethylenic or polyethylenic crosslinking monomer (AR);
- the sum of said molar proportions of monomer units according to $a_1$) and $a_2$) being equal to 100 mol %;

said self-invertible inverse latex being an emulsion of water-in-oil (W) comprising, per 100% of its weight:
- a)—from 10% by weight to 90% by weight of said crosslinked anionic polyelectrolyte (P);
- b)—from 5% by weight to 50% by weight of a fatty phase constituted of at least one oil (O);
- c)—from 1% by weight to 50% by weight of water;
- d)—from 0.5% by weight to 10% by weight of an emulsifying system of water-in-oil ($S_1$); and
- e)—from 2% by weight to 10% by weight of an emulsifying system of oil-in-water ($S_2$);
- the sum of the proportions by weight of a), b), c), d) and e) being equal to 100% by weight;

wherein said emulsifying system of oil-in-water ($S_2$) comprises, per 100% of its weight:
- f)—a proportion of greater than or equal to 50% by weight and less than or equal to 100% of a composition ($C_e$) which comprises, per 100% of its weight;
- $e_1$)—from 5% by weight to 15% by weight of at least one compound of formula (I):

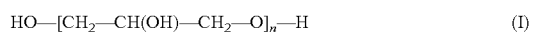

in which n represents an integer greater than or equal to 1 and less than or equal to 15; and
- $e_2$)—from 60% by weight to 80% by weight of at least one compound of formula (II):

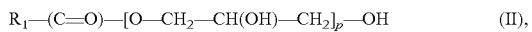

in which p, which is different from or identical to n, represents an integer greater than or equal to 1 and less than or equal to 15; and in which the $R_1$—(C=O)— group represents a saturated or unsaturated and linear or branched aliphatic radical comprising from 6 to 22 carbon atoms; and
- $e_3$)—from 5% to 15% by weight of at least one composition ($C_{11}$) represented by the formula (III):

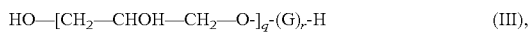

in which formula (III) q, which is different from or identical to n, represents an integer greater than or equal to 1 and less than or equal to 3, G represents the residue of a reducing sugar and r represents a decimal number greater than or equal to 1.05 and less than or equal to 5.00, said composition ($C_{11}$) consisting of a mixture of the compounds of formulae ($III_1$), ($III_2$), ($III_3$), ($III_4$) and ($III_5$):

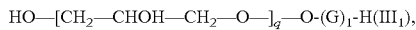

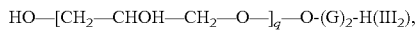

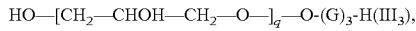

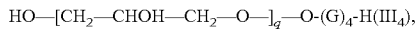

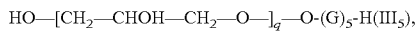

in molar proportions of said compounds of formulae ($III_1$), ($III_2$), ($III_3$), ($III_4$) and ($III_5$) respectively equal to $a_1$, $a_2$, $a_3$, $a_4$ and $a_5$, such that the sum $a_1+a_2+a_3+a_4+a_5$ is equal to 1, and that the sum $a_1+2a_2+3a_3+4a_4+5a_5$ is equal to r; the sum of the proportions by weight of $e_1$), $e_2$) and $e_3$) being equal to 100% by weight.

8. A thickening and/or emulsifying and/or stabilizing agent for a topical cosmetic composition, comprising said self-invertible inverse latex as defined in claim 1.

9. A topical cosmetic composition (F), comprising, as thickening agent, per 100% of its total weight, between 0.1% and 10% by weight of said self-invertible inverse latex as defined in claim 1.

10. A topical pharmaceutical composition (G), comprising, as thickening agent, per 100% of its total weight, between 0.1% and 10% by weight of said self-invertible inverse latex as defined in claim 1.

* * * * *